(12) United States Patent
Miyamoto et al.

(10) Patent No.: US 8,546,113 B2
(45) Date of Patent: Oct. 1, 2013

(54) HYDROGEN PEROXIDE-FORMING NADH OXIDASE AND DNA ENCODING THE SAME

(75) Inventors: Kenji Miyamoto, Kanagawa (JP); Hiromichi Ohta, Kanagawa (JP)

(73) Assignee: Keio University, Tokyo (JP)

( * ) Notice: Subject to any disclaimer, the term of this patent is extended or adjusted under 35 U.S.C. 154(b) by 375 days.

(21) Appl. No.: 12/863,555

(22) PCT Filed: Jan. 9, 2009

(86) PCT No.: PCT/JP2009/050601
§ 371 (c)(1), (2), (4) Date: Oct. 6, 2010

(87) PCT Pub. No.: WO2009/091054
PCT Pub. Date: Jul. 23, 2009

(65) Prior Publication Data
US 2011/0045548 A1 Feb. 24, 2011

(30) Foreign Application Priority Data

Jan. 17, 2008 (JP) ................. 2008-008062

(51) Int. Cl.
*C12P 13/22* (2006.01)
*C12P 7/42* (2006.01)
*C12N 9/02* (2006.01)
*C07H 21/04* (2006.01)
*C07K 1/00* (2006.01)

(52) U.S. Cl.
USPC .......... 435/108; 435/146; 435/189; 536/23.2; 530/350

(58) Field of Classification Search
USPC ......... 435/108, 146, 189; 536/23.2; 530/350
See application file for complete search history.

(56) References Cited

U.S. PATENT DOCUMENTS

| 4,954,445 A | 9/1990 | Yoshihama et al. |
| 5,514,587 A | 5/1996 | Higuchi et al. |
| 6,987,013 B2 | 1/2006 | Hummel et al. |

FOREIGN PATENT DOCUMENTS

| EP | 0 623 677 | 11/1994 |
| EP | 1 285 962 | 2/2003 |
| JP | 63 44882 | 2/1988 |
| JP | 2 107186 | 4/1990 |
| JP | 0 385 415 | 9/1990 |
| JP | 4 365478 | 12/1992 |
| JP | 5 84072 | 4/1993 |
| JP | 5 344890 | 12/1993 |
| JP | 7 163378 | 6/1995 |
| JP | 8 196281 | 8/1996 |
| JP | 2003 116585 | 4/2003 |
| JP | 2008 92832 | 4/2008 |
| WO | 2004 011670 | 2/2004 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Miyamoto, Kenji et al., "Effiecient oxidation of alcohols by a 2-phenylethanol-degrading *Brevibacterium* sp.", Biotechnology Letters, vol. 26, No. 17, pp. 1385-1388, (Sep. 2004).
Hirano, Jun-ichiro et al., "Purification and characterization of thermostable $H_2O_2$-forming NADH oxidase from 2-phenylethanol-assimilating *Brevibacterium* sp. KU1309", Appl., Microbiol., Biotechnol., vol. 80, No. 1, pp. 71-78, (Aug. 2008).
Extended Search Report issued Jun. 1, 2011 in Europe Application No. 09703037.3.
Takashi Murachi, et al., "A flow injection analysis system involving immobilized NADH oxidase in column form for clinical analysis", Journal of Biotechnology, vol. 14, No. 1, Apr. 1, 1990, pp. 33-41.
Jun-Ichiro Hirano, et al., "Purification and characterization of NADH oxidase from 2-phenylethanol-assimilating *Brevibacterium* sp. KU1309", Journal of Molecular Catalysis B: Enzymatic, vol. 48, No. 3-4, Sep. 24, 2007. p. 108.
Kumiko Fujimori, et al., "Cloning and expression of a novel NADH oxidase gene from *Brevibacterium* sp. KU1309", Journal of Molecular Catalysis B: Enzymatic, vol. 62, No. 1, Jan. 2, 2010, pp. 124-125.
Office Action as received in the corresponding European Patent Application No. 09 703 037.3-1410 dated Feb. 19, 2013 (English Translation Only).
Jun-ichiro Hirano, et al., "Purification and characterization of aldehyde dehydrogenase with a broad substrate specificity originated from 2-phenylethanol-assimilating *Brevibacterium* sp. KU1309" Appl. Microbiol Biotechnol (2007) 76:357-363.

* cited by examiner

*Primary Examiner* — Ganapathirama Raghu
(74) *Attorney, Agent, or Firm* — Oblon, Spivak, McClelland, Maier & Neustadt, L.L.P.

(57) ABSTRACT

It is an object of the present invention to provide DNA encoding novel NADH oxidase from a microorganism belonging to the genus *Brevibacterium* having excellent pH stability and thermostability. The present invention relates to DNA encoding NADH oxidase from a microorganism belonging to the genus *Brevibacterium* that is the following (a) or (b):
(a) NADH oxidase comprising the amino acid sequence of SEQ ID NO: 18; or
(b) NADH oxidase comprising an amino acid sequence derived from the amino acid sequence of SEQ ID NO: 18 by deletion, substitution, or addition of 1 or more amino acid(s) and having NADH oxidase activity.

1 Claim, 21 Drawing Sheets

The farthest left lane represents a perfect protein marker (NOVAGEN). 1: Cell-free extract; 2: Ammonium sulfate fractionation; 3: Phenyl toyopearl; 4: DEAE toyoperal; 5: Butyl toyopearl; and 6: Butyl toyoperal (with the increased amount)

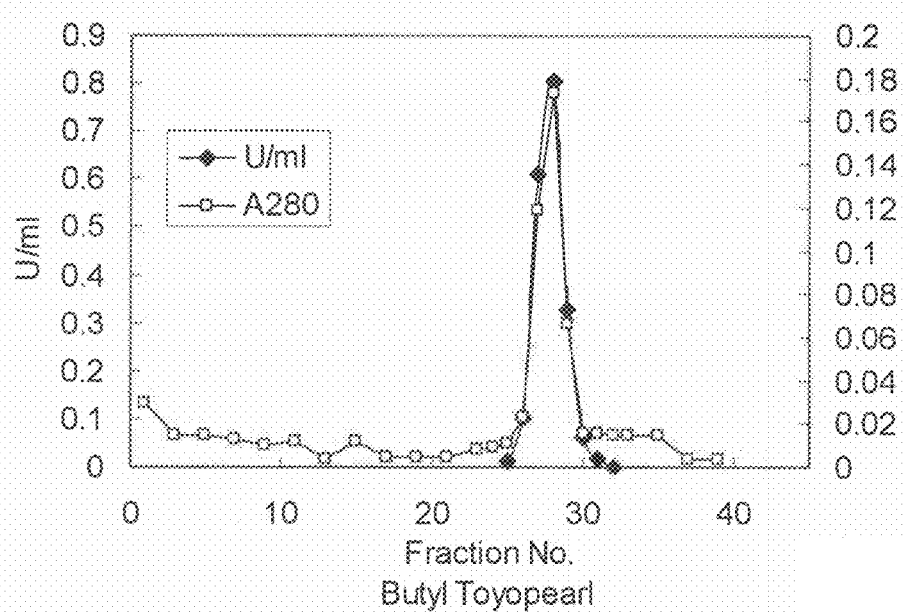

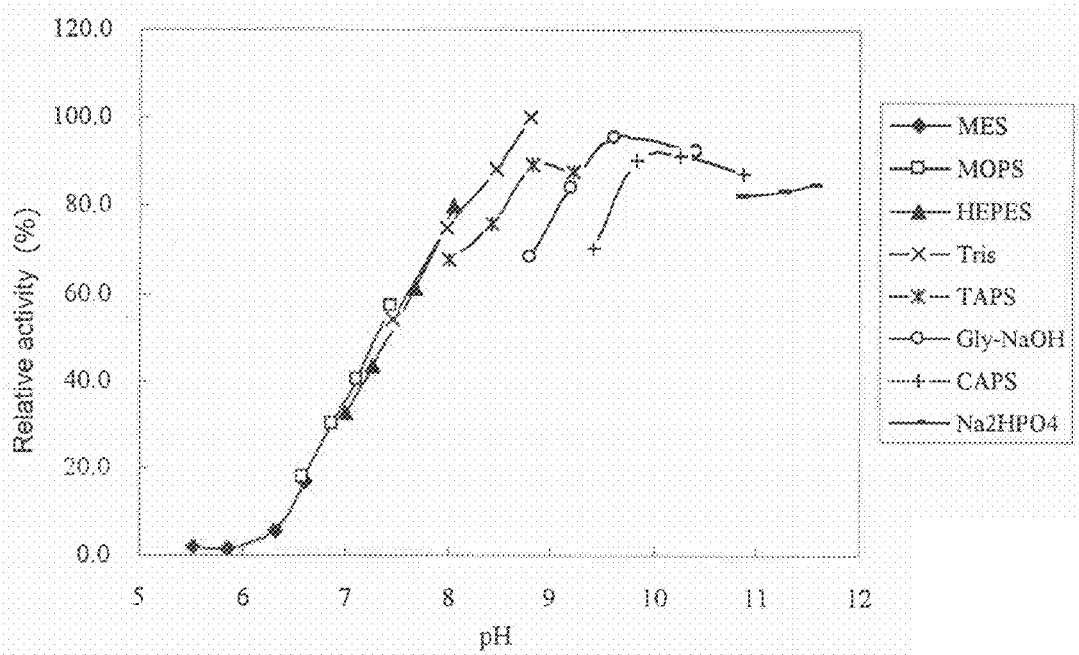

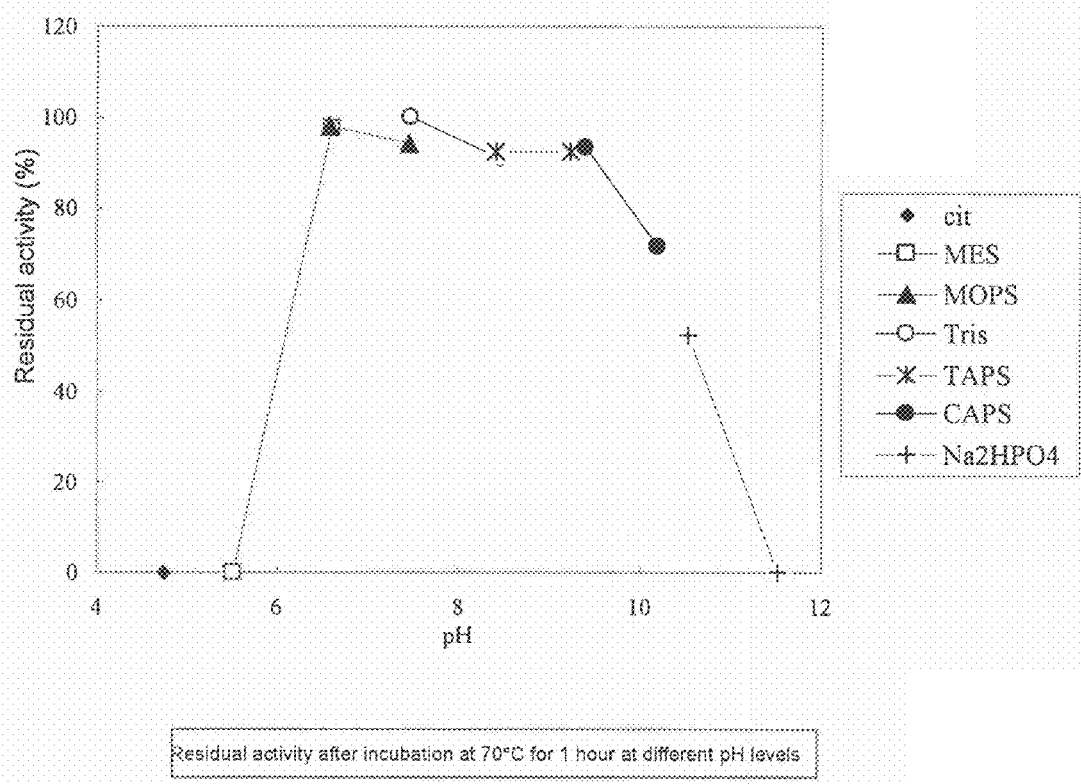

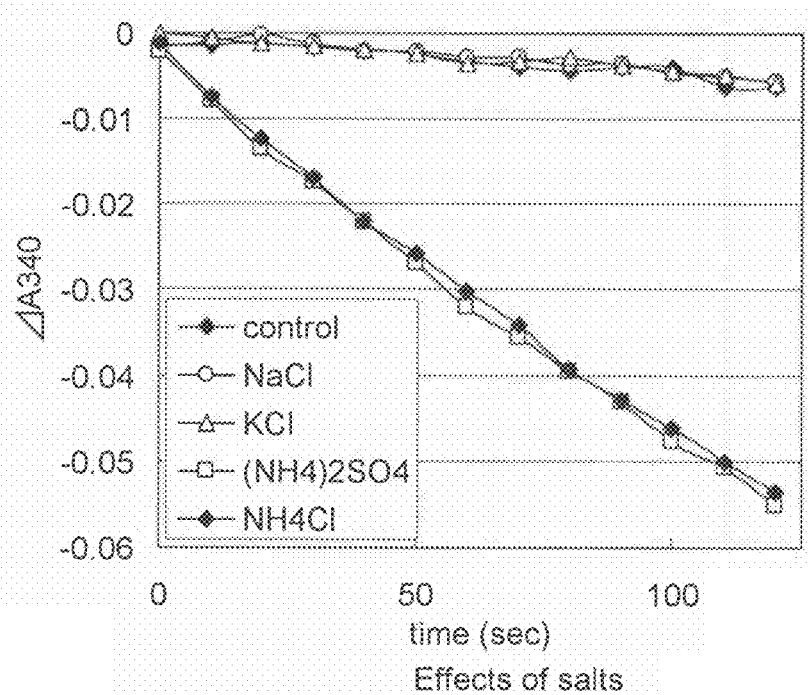

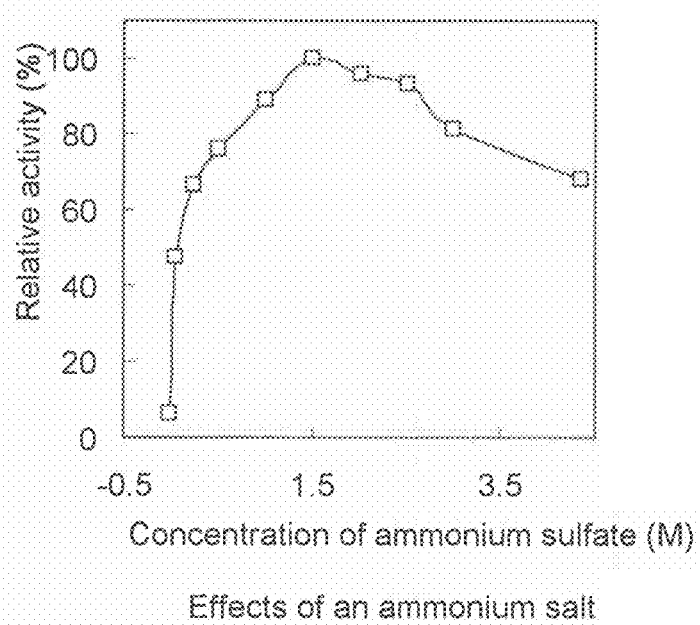

Fig. 6

|  | Compounds | Relative activity (%) |
|---|---|---|
| Metal ion | BaCl$_2$ | 106 |
|  | MnCl$_2$ | 101 |
|  | MgCl$_2$ | 97 |
|  | NiCl$_2$ | 102 |
|  | ZnCl$_2$ | 39 |
|  | CuCl$_2$ | 42 |
|  | HgCl$_2$ | 71 |
|  | AgNO$_3$ | 37 |
| Carbonyl reagent | NaN$_3$ | 97 |
| Metal chelating reagent | EDTA | 110 |
|  | 8-quinolinol | 107 |
| SH reagent | N-ethylmaleimide | 110 |
|  | Iodide acetate | 105 |
|  | Iodide acetamide | 101 |
|  | p-CMBA | 187 |
| OH reagent | PMSF | 99 |

Determination of residual activity after incubation for 3 min. in the presence of different compounds (1 mM each)

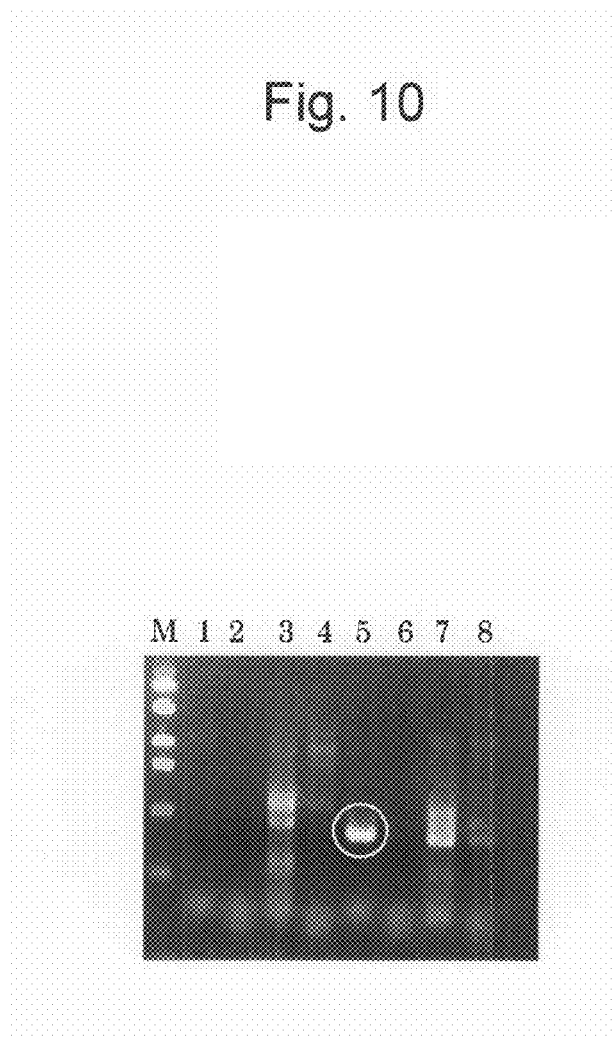

Fig. 13A

GTGATGATGCCCACCTGTGTCCAATCAGACAGCGTTTTTCTTCGCCCCGCGCAAGAAAAG
TGGAAAGATAAGACTGAAAGCTGCGTACTGCAGGCTTATTCACAGCTACGAGGAGAAATCC

| | | | | | | | | | | | | | | | | |
|---|---|---|---|---|---|---|---|---|---|---|---|---|---|---|---|---|
| 1 | GTG | AGT | GAC | GAA | TTG | ACC | TAC | GAC | CTT | GTC | GTT | CTG | GGT | GGC | GGA | 45 |
| 1 | Val | Ser | Asp | Glu | Leu | Thr | Tyr | Asp | Leu | Val | Val | Leu | Gly | Gly | Gly | 15 |
| 46 | ACC | GGT | GGC | TAT | GCC | GCT | GCT | CTG | CGA | GCC | GCA | GAG | CTC | GAC | ATG | 90 |
| 16 | Thr | Gly | Gly | Tyr | Ala | Ala | Ala | Leu | Arg | Ala | Ala | Glu | Leu | Asp | Met | 30 |
| 91 | AAG | GTC | GCT | TTG | ATC | GAA | CGC | GAC | AAG | GTG | GGA | GGC | ACC | TGC | CTG | 135 |
| 31 | Lys | Val | Ala | Leu | Ile | Glu | Arg | Asp | Lys | Val | Gly | Gly | Thr | Cys | Leu | 45 |
| 136 | CAC | CGT | GGC | TGC | GTT | CCG | ACG | AAG | GCT | CTT | CTG | CAC | GCC | GCA | GAA | 180 |
| 46 | His | Arg | Gly | Cys | Val | Pro | Thr | Lys | Ala | Leu | Leu | His | Ala | Ala | Glu | 60 |
| 181 | GTC | GCC | GAG | ACC | GCC | AAG | AAC | TCC | GAG | ACC | TTC | GGC | ATC | GAA | GCC | 225 |
| 61 | Val | Ala | Glu | Thr | Ala | Lys | Asn | Ser | Glu | Thr | Phe | Gly | Ile | Glu | Ala | 75 |
| 226 | GAG | TTA | CAG | GGG | ATC | GAC | ATC | GCC | AAG | GTG | CTC | GAG | TAC | AAG | GAC | 270 |
| 76 | Glu | Leu | Gln | Gly | Ile | Asp | Ile | Ala | Lys | Val | Leu | Glu | Tyr | Lys | Asp | 90 |
| 271 | GGG | GTC | ATC | ACC | CGC | AAC | TAC | AAG | GGT | CTG | CAG | GGT | CTG | GTC | AAG | 315 |
| 91 | Gly | Val | Ile | Thr | Arg | Asn | Tyr | Lys | Gly | Leu | Gln | Gly | Leu | Val | Lys | 105 |
| 316 | GCT | CGC | GGA | ATC | GAC | ACC | TAC | TTC | GGC | ACC | GGC | AAG | CTC | GTC | GGC | 360 |
| 106 | Ala | Arg | Gly | Ile | Asp | Thr | Tyr | Phe | Gly | Thr | Gly | Lys | Leu | Val | Gly | 120 |
| 361 | AAA | GAC | ACT | GTC | GAG | GTC | ACC | GGC | GAA | GAC | GGC | AAC | CAC | ACC | GTC | 405 |
| 121 | Lys | Asp | Thr | Val | Glu | Val | Thr | Gly | Glu | Asp | Gly | Asn | His | Thr | Val | 135 |
| 406 | AAG | GGC | ACG | AAC | GTT | CTG | CTC | TCG | ACC | GGT | TCG | ACA | TCG | AAG | ACC | 450 |
| 136 | Lys | Gly | Thr | Asn | Val | Leu | Leu | Ser | Thr | Gly | Ser | Thr | Ser | Lys | Thr | 150 |

Fig. 13B

```
451   ATC GGA CTC GAG GTC ACC GAC CGC GTG ATC ACG AGC ACC GAG GCT   495
151   Ile Gly Leu Glu Val Thr Asp Arg Val Ile Thr Ser Thr Glu Ala   165

496   CTC CAA CTC GAC AAG GTC CCG AGC TCG GCC ATC GTG CTC GGC GGC   540
166   Leu Gln Leu Asp Lys Val Pro Ser Ser Ala Ile Val Leu Gly Gly   180

541   GGC GTC ATC GGC GTC GAG TTC GCC AGC GTC TGG AAC TCC TTC GGA   585
181   Gly Val Ile Gly Val Glu Phe Ala Ser Val Trp Asn Ser Phe Gly   195

586   GCT GAG GTC ACG ATC GTC GAG GGC CTC AAG CAC CTC GTT GCC AAC   630
196   Ala Glu Val Thr Ile Val Glu Gly Leu Lys His Leu Val Ala Asn   210

631   GAG GAC GAG ACC ATC TCG AAG AAC CTC GAG CGC GCC TTC AAG AAG   675
211   Glu Asp Glu Thr Ile Ser Lys Asn Leu Glu Arg Ala Phe Lys Lys   225

676   CGC AAG ATC AAG TTC AAG CTC GGC GTC ATG TTC AAG GGC GTC GAA   720
226   Arg Lys Ile Lys Phe Lys Leu Gly Val Met Phe Lys Gly Val Glu   240

721   GAG ACG GCC GAC GGG GTC AAG GTC ACT CTC GAA GAC GGT TCG ACG   765
241   Glu Thr Ala Asp Gly Val Lys Val Thr Leu Glu Asp Gly Ser Thr   255

766   CTC GAG GCG GAG TAC CTC CTC GTG GCG GTC GGC CGC GGC CCG GTC   810
256   Leu Glu Ala Glu Tyr Leu Leu Val Ala Val Gly Arg Gly Pro Val   270

811   ACC GAG GGC TTC GGC TTC GAA GAG CAG GGT ATC CCG ATG GAT CGC   855
271   Thr Glu Gly Phe Gly Phe Glu Glu Gln Gly Ile Pro Met Asp Arg   285

856   GGA TTC GTC CTC GCC AGC GAA CGT CTC CAC ACC GGC GTC GGC AAC   900
286   Gly Phe Val Leu Ala Ser Glu Arg Leu His Thr Gly Val Gly Asn   300

901   ATC TAC GCC TGC GGC GAT ATC GTC CCC GGA CTC CAA CTG GCC CAC   945
301   Ile Tyr Ala Cys Gly Asp Ile Val Pro Gly Leu Gln Leu Ala His   315
```

Fig. 13C

```
946   CGC GCC TTC GGC CAG GGC ATC TTC ATC GCC GAG GAG ATC GCT GGA   990
316   Arg Ala Phe Gly Gln Gly Ile Phe Ile Ala Glu Glu Ile Ala Gly   330

991   CTC AAC CCG GCA CCG GTC GTC GAA TCC GGC ATC CCC CGC GTA ACC   1035
331   Leu Asn Pro Ala Pro Val Val Glu Ser Gly Ile Pro Arg Val Thr   345

1036  TAC TGC GAA CCG GAG ATC TTC TCC GTC GGA CTC TCC TCT GCA CAG   1080
346   Tyr Cys Glu Pro Glu Ile Phe Ser Val Gly Leu Ser Ser Ala Gln   360

1081  GCG GAA GAG AAG TAC GGC AAG GAT CAG GTC GAA TCG CTC GAG TAC   1125
361   Ala Glu Glu Lys Tyr Gly Lys Asp Gln Val Glu Ser Leu Glu Tyr   375

1126  AAC CTC GGC GGC AAC GGC AAG TCC GTG ATC CTG AAC ACG ACA GGT   1170
376   Asn Leu Gly Gly Asn Gly Lys Ser Val Ile Leu Asn Thr Thr Gly   390

1171  CTG ATC AAG GTC ATC CGC GAA AAG GAC GGT CCG GTC GTC GGC GTC   1215
391   Leu Ile Lys Val Ile Arg Glu Lys Asp Gly Pro Val Val Gly Val   405

1216  CAC GGA ATC GGT GCT CGT CTG TCC GAG CAG GCC GGT GAA GCT CAG   1260
406   His Gly Ile Gly Ala Arg Leu Ser Glu Gln Ala Gly Glu Ala Gln   420

1261  CTC ATC GTC AAT TGG GAA GCA TTC CCC GAG GAA GTC GCG CAG CTC   1305
421   Leu Ile Val Asn Trp Glu Ala Phe Pro Glu Glu Val Ala Gln Leu   435

1306  ATC CAC GCG CAC CCC ACG CAG AAC GAA GCA CTC GGC GAG GCC CAC   1350
436   Ile His Ala His Pro Thr Gln Asn Glu Ala Leu Gly Glu Ala His   450

1351  CTG GCC CTG GCC GGC AAA CCC CTG CAC TTC CAC TCA TAA   1389
451   Leu Ala Leu Ala Gly Lys Pro Leu His Phe His Ser End
GATCCGAGGAGACGAATACTCATGTTTAATTCCGTTCAGATGCCGGCTCTCGGAGAGTCGGTCACCG
AGGGCACTGTCACTCGCTGGCTCAAGGAAAGTGGGCGAAGAA
```

Fig. 14
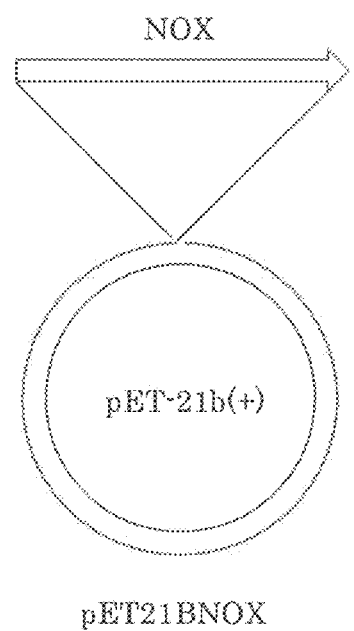
pET21BNOX
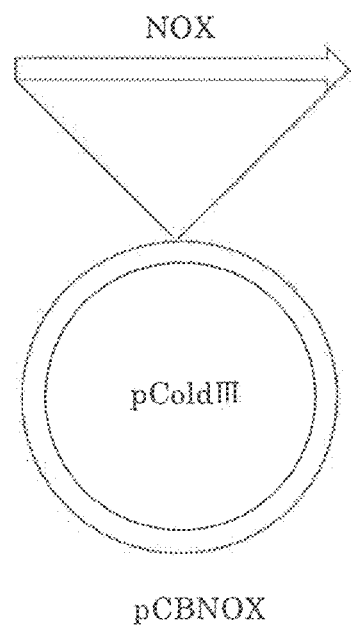
pCBNOX

SEQUENCE LISTING

```
<160> NUMBER OF SEQ ID NOS: 20

<210> SEQ ID NO 1
<211> LENGTH: 507
<212> TYPE: DNA
<213> ORGANISM: Brevibacterium sp.

<400> SEQUENCE: 1
tggagagttt gatcctggct caggacgaac gctggctgcg tgcttaacac atgcaagtcg      60
aacgctgaag ccgacagctt gctgttggtg gatgagtggc gaacgggtga gtaacacgtg     120
agtaacctgc ccctgatttc gggataagcc tgggaaaccg ggtctaatac cggatacgac     180
catccctcgc atgagggttg gtggaaagtt tttcgatcgg ggatgggctc gcggcctatc     240
agcttgttgg tggggtaatg gcctaccaag gcgacgacgg gtagccggcc tgagagggcg     300
accggccaca ctgggactga gacacggccc agactcctac gggaggcagc agtggggaat     360
attgcacaat gggggaaacc ctgatgcagc gacgcagcgt gcgggatgac ggccttcggg     420
ttgtaaaccg ctttcagcag ggaagaagcg aaagtgacgg tacctgcaga agaagtaccg     480
gctaactacg tgccagcagc cgcggta                                         507

<210> SEQ ID NO 2
<211> LENGTH: 17
<212> TYPE: PRT
<213> ORGANISM: Brevibacterium sp.
<220> FEATURE:
<221> NAME/KEY: MOD_RES
<222> LOCATION: (1)..(1)
```

-continued

<223> OTHER INFORMATION: Any naturally occurring amino acid

<400> SEQUENCE: 2

Xaa Asp Glu Leu Thr Tyr Asp Leu Val Val Leu Gly Gly Gly Thr Gly
1               5                   10                  15

Gly

<210> SEQ ID NO 3
<211> LENGTH: 18
<212> TYPE: PRT
<213> ORGANISM: Brevibacterium sp.

<400> SEQUENCE: 3

Gly Pro Val Thr Glu Gly Phe Gly Phe Glu Glu Gln Gly Ile Pro Met
1               5                   10                  15

Asp Arg

<210> SEQ ID NO 4
<211> LENGTH: 10
<212> TYPE: PRT
<213> ORGANISM: Brevibacterium sp.

<400> SEQUENCE: 4

Asp Glu Leu Thr Tyr Asp Leu Val Val Leu
1               5                   10

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: Inosine
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (21)..(21)
<223> OTHER INFORMATION: Inosine
<220> FEATURE:
<221> NAME/KEY: modified_base
<222> LOCATION: (24)..(24)
<223> OTHER INFORMATION: Inosine
<220> FEATURE:
<221> NAME/KEY: modified_base
<222> LOCATION: (27)..(27)
<223> OTHER INFORMATION: a, c, t, g, unknown or other

<400> SEQUENCE: 5
gaygarytna cntaygayyt ngtngtnyt                                29

<210> SEQ ID NO 6
<211> LENGTH: 9
<212> TYPE: PRT
<213> ORGANISM: Brevibacterium sp.

<400> SEQUENCE: 6

Val Leu Gly Gly Gly Thr Gly Gly Tyr
1               5

<210> SEQ ID NO 7
<211> LENGTH: 26

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: Inosine
<220> FEATURE:
<221> NAME/KEY: modified_base
<222> LOCATION: (21)..(21)
<223> OTHER INFORMATION: Inosine
<220> FEATURE:
<221> NAME/KEY: modified_base
<222> LOCATION: (24)..(24)
<223> OTHER INFORMATION: a, c, t, g, unknown or other

<400> SEQUENCE: 7
aarytnggng gnggnacngg nggnta                                      26

<210> SEQ ID NO 8
<211> LENGTH: 9
<212> TYPE: PRT
<213> ORGANISM: Brevibacterium sp.

<400> SEQUENCE: 8

Pro Val Thr Glu Gly Phe Gly Phe Glu
1               5

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (12)..(12)
<223> OTHER INFORMATION: Inosine
<220> FEATURE:
<221> NAME/KEY: modified_base
<222> LOCATION: (18)..(18)
<223> OTHER INFORMATION: Inosine
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 9
```
tcraanccra anccytcngt nacngg                                          26

<210> SEQ ID NO 10
<211> LENGTH: 9
<212> TYPE: PRT
<213> ORGANISM: Brevibacterium sp.

<400> SEQUENCE: 10

Thr Glu Gly Phe Gly Phe Glu Glu Gln
1               5

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (12)..(12)
<223> OTHER INFORMATION: a, c, t, g, unknown or other

<400> SEQUENCE: 11
tccatnggda tnccytgytc ytcraa                                          26

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acggtgcagg caggtgcctc ccaccttgtc                                      30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgttcgatc aaagcgacct tcatgtcgag                                      30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggcgtcatgt tcaagggcgt cgaagagacg                                      30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic -continued primer
<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gccgacgggg tcaaggtcac tctcgaagac                                      30

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
tccgtcggac tctcctctgc acag                                            24

<210> SEQ ID NO 17
<211> LENGTH: 1619
<212> TYPE: DNA
<213> ORGANISM: Brevibacterium sp.
<220> FEATURE:
<221> NAME/KEY: CDS
<222> LOCATION: (122)..(1507)

<400> SEQUENCE: 17

```
gtgatgatgc ccacctgtgt ccaatcagac agcgttttc ttcgcccgc gcaagaaaag      60 tggaaagata agactgaaag ctgcgtactg caggcttatt cacagctacg aggagaaatc   120 c gtg agt gac gaa ttg acc tac gac ctt gtc gtt ctg ggt ggc gga acc   169
  Val Ser Asp Glu Leu Thr Tyr Asp Leu Val Val Leu Gly Gly Gly Thr
  1               5                  10                   15 ggt ggc tat gcc gct gct ctg cga gcc gca gag ctc gac atg aag gtc   217
Gly Gly Tyr Ala Ala Ala Leu Arg Ala Ala Glu Leu Asp Met Lys Val
             20                  25                  30 gct ttg atc gaa cgc gac aag gtg gga ggc acc tgc ctg cac cgt ggc   265
Ala Leu Ile Glu Arg Asp Lys Val Gly Gly Thr Cys Leu His Arg Gly
         35                  40                  45 tgc gtt ccg acg aag gct ctt ctg cac gcc gca gaa gtc gcc gag acc   313
Cys Val Pro Thr Lys Ala Leu Leu His Ala Ala Glu Val Ala Glu Thr
     50                  55                  60 gcc aag aac tcc gag acc ttc ggc atc gaa gcc gag tta cag ggg atc   361
Ala Lys Asn Ser Glu Thr Phe Gly Ile Glu Ala Glu Leu Gln Gly Ile
65                  70                  75                  80 gac atc gcc aag gtg ctc gag tac aag gac ggg gtc atc acc cgc aac   409
Asp Ile Ala Lys Val Leu Glu Tyr Lys Asp Gly Val Ile Thr Arg Asn
                 85                  90                  95 tac aag ggt ctg cag ggt ctg gtc aag gct cgc gga atc gac acc tac   457
Tyr Lys Gly Leu Gln Gly Leu Val Lys Ala Arg Gly Ile Asp Thr Tyr
            100                 105                 110 ttc ggc acc ggc aag ctc gtc ggc aaa gac act gtc gag gtc acc ggc   505
Phe Gly Thr Gly Lys Leu Val Gly Lys Asp Thr Val Glu Val Thr Gly
        115                 120                 125 gaa gac ggc aac cac acc gtc aag ggc acg aac gtt ctg ctc tcg acc   553
Glu Asp Gly Asn His Thr Val Lys Gly Thr Asn Val Leu Leu Ser Thr
    130                 135                 140 ggt tcg aca tcg aag acc atc gga ctc gag gtc acc gac cgc gtg atc   601
Gly Ser Thr Ser Lys Thr Ile Gly Leu Glu Val Thr Asp Arg Val Ile
145                 150                 155                 160 acg agc acc gag gct ctc caa ctc gac aag gtc ccg agc tcg gcc atc   649
Thr Ser Thr Glu Ala Leu Gln Leu Asp Lys Val Pro Ser Ser Ala Ile
                165                 170                 175 gtg ctc ggc ggc ggc gtc atc ggc gtc gag ttc gcc agc gtc tgg aac   697
Val Leu Gly Gly Gly Val Ile Gly Val Glu Phe Ala Ser Val Trp Asn
```

```
                      180               185               190
tcc ttc gga gct gag gtc acg atc gtc gag ggc ctc aag cac ctc gtt      745
Ser Phe Gly Ala Glu Val Thr Ile Val Glu Gly Leu Lys His Leu Val
    195               200               205 gcc aac gag gac gag acc atc tcg aag aac ctc gag cgc gcc ttc aag      793
Ala Asn Glu Asp Glu Thr Ile Ser Lys Asn Leu Glu Arg Ala Phe Lys
210               215               220 aag cgc aag atc aag ttc aag ctc ggc gtc atg ttc aag ggc gtc gaa      841
Lys Arg Lys Ile Lys Phe Lys Leu Gly Val Met Phe Lys Gly Val Glu
225               230               235               240 gag acg gcc gac ggg gtc aag gtc act ctc gaa gac ggt tcg acg ctc      889
Glu Thr Ala Asp Gly Val Lys Val Thr Leu Glu Asp Gly Ser Thr Leu
                245               250               255 gag gcg gag tac ctc ctc gtg gcg gtc ggc cgc ggc ccg gtc acc gag      937
Glu Ala Glu Tyr Leu Leu Val Ala Val Gly Arg Gly Pro Val Thr Glu
            260               265               270 ggc ttc ggc ttc gaa gag cag ggt atc ccg atg gat cgc gga ttc gtc      985
Gly Phe Gly Phe Glu Glu Gln Gly Ile Pro Met Asp Arg Gly Phe Val
        275               280               285 ctc gcc agc gaa cgt ctc cac acc ggc gtc ggc aac atc tac gcc tgc     1033
Leu Ala Ser Glu Arg Leu His Thr Gly Val Gly Asn Ile Tyr Ala Cys
    290               295               300 ggc gat atc gtc ccc gga ctc caa ctg gcc cac cgc gcc ttc ggc cag     1081
Gly Asp Ile Val Pro Gly Leu Gln Leu Ala His Arg Ala Phe Gly Gln
305               310               315               320 ggc atc ttc atc gcc gag gag atc gct gga ctc aac ccg gca ccg gtc     1129
Gly Ile Phe Ile Ala Glu Glu Ile Ala Gly Leu Asn Pro Ala Pro Val
                325               330               335 gtc gaa tcc ggc atc ccc cgc gta acc tac tgc gaa ccg gag atc ttc     1177
Val Glu Ser Gly Ile Pro Arg Val Thr Tyr Cys Glu Pro Glu Ile Phe
            340               345               350 tcc gtc gga ctc tcc tct gca cag gcg gaa gag aag tac ggc aag gat     1225
Ser Val Gly Leu Ser Ser Ala Gln Ala Glu Glu Lys Tyr Gly Lys Asp
        355               360               365 cag gtc gaa tcg ctc gag tac aac ctc ggc ggc aac ggc aag tcc gtg     1273
Gln Val Glu Ser Leu Glu Tyr Asn Leu Gly Gly Asn Gly Lys Ser Val
    370               375               380 atc ctg aac acg aca ggt ctg atc aag gtc atc cgc gaa aag gac ggt     1321
Ile Leu Asn Thr Thr Gly Leu Ile Lys Val Ile Arg Glu Lys Asp Gly
385               390               395               400 ccg gtc gtg ggc gtg cac gga atc ggt gct cgt ctg tcc gag cag gcc     1369
Pro Val Val Gly Val His Gly Ile Gly Ala Arg Leu Ser Glu Gln Ala
                405               410               415 ggt gaa gct cag ctc atc gtc aat tgg gaa gca ttc ccc gag gaa gtc     1417
Gly Glu Ala Gln Leu Ile Val Asn Trp Glu Ala Phe Pro Glu Glu Val
            420               425               430 gcg cag ctc atc cac gcg cac ccc acg cag aac gaa gca ctc ggc gag     1465
Ala Gln Leu Ile His Ala His Pro Thr Gln Asn Glu Ala Leu Gly Glu
        435               440               445 gcc cac ctg gcc ctg gcc ggc aaa ccc ctg cac ttc cac tca              1507
Ala His Leu Ala Leu Ala Gly Lys Pro Leu His Phe His Ser
    450               455               460 taagatccga ggagacgaat actcatgttt aattccgttc agatgccggc tctcggagag   1567
tcggtcaccg agggcactgt cactcgctgg ctcaaggaaa gtgggcgaag aa           1619

<210> SEQ ID NO 18
<211> LENGTH: 462
<212> TYPE: PRT
<213> ORGANISM: Brevibacterium sp.
```

<400> SEQUENCE: 18

```
Val Ser Asp Glu Leu Thr Tyr Asp Leu Val Val Leu Gly Gly Gly Thr
1               5                   10                  15

Gly Gly Tyr Ala Ala Ala Leu Arg Ala Ala Glu Leu Asp Met Lys Val
            20                  25                  30

Ala Leu Ile Glu Arg Asp Lys Val Gly Gly Thr Cys Leu His Arg Gly
        35                  40                  45

Cys Val Pro Thr Lys Ala Leu Leu His Ala Ala Glu Val Ala Glu Thr
    50                  55                  60

Ala Lys Asn Ser Glu Thr Phe Gly Ile Glu Ala Glu Leu Gln Gly Ile
65              70                  75                  80

Asp Ile Ala Lys Val Leu Glu Tyr Lys Asp Gly Val Ile Thr Arg Asn
                85                  90                  95

Tyr Lys Gly Leu Gln Gly Leu Val Lys Ala Arg Gly Ile Asp Thr Tyr
            100                 105                 110

Phe Gly Thr Gly Lys Leu Val Gly Lys Asp Thr Val Glu Val Thr Gly
        115                 120                 125

Glu Asp Gly Asn His Thr Val Lys Gly Thr Asn Val Leu Leu Ser Thr
130                 135                 140

Gly Ser Thr Ser Lys Thr Ile Gly Leu Glu Val Thr Asp Arg Val Ile
145             150                 155                 160

Thr Ser Thr Glu Ala Leu Gln Leu Asp Lys Val Pro Ser Ser Ala Ile
                165                 170                 175

Val Leu Gly Gly Gly Val Ile Gly Val Glu Phe Ala Ser Val Trp Asn
            180                 185                 190

Ser Phe Gly Ala Glu Val Thr Ile Val Glu Gly Leu Lys His Leu Val
        195                 200                 205

Ala Asn Glu Asp Glu Thr Ile Ser Lys Asn Leu Glu Arg Ala Phe Lys
    210                 215                 220

Lys Arg Lys Ile Lys Phe Lys Leu Gly Val Met Phe Lys Gly Val Glu
225                 230                 235                 240

Glu Thr Ala Asp Gly Val Lys Val Thr Leu Glu Asp Gly Ser Thr Leu
                245                 250                 255

Glu Ala Glu Tyr Leu Leu Val Ala Val Gly Arg Gly Pro Val Thr Glu
            260                 265                 270

Gly Phe Gly Phe Glu Glu Gln Gly Ile Pro Met Asp Arg Gly Phe Val
        275                 280                 285

Leu Ala Ser Glu Arg Leu His Thr Gly Val Gly Asn Ile Tyr Ala Cys
    290                 295                 300

Gly Asp Ile Val Pro Gly Leu Gln Leu Ala His Arg Ala Phe Gly Gln
305                 310                 315                 320

Gly Ile Phe Ile Ala Glu Glu Ile Ala Gly Leu Asn Pro Ala Pro Val
                325                 330                 335

Val Glu Ser Gly Ile Pro Arg Val Thr Tyr Cys Glu Pro Glu Ile Phe
            340                 345                 350

Ser Val Gly Leu Ser Ser Ala Gln Ala Glu Glu Lys Tyr Gly Lys Asp
        355                 360                 365

Gln Val Glu Ser Leu Glu Tyr Asn Leu Gly Gly Asn Gly Lys Ser Val
    370                 375                 380

Ile Leu Asn Thr Thr Gly Leu Ile Lys Val Ile Arg Glu Lys Asp Gly
385                 390                 395                 400

Pro Val Val Gly Val His Gly Ile Gly Ala Arg Leu Ser Glu Gln Ala
                405                 410                 415
```

```
Gly Glu Ala Gln Leu Ile Val Asn Trp Glu Ala Phe Pro Glu Glu Val
            420                 425                 430

Ala Gln Leu Ile His Ala His Pro Thr Gln Asn Glu Ala Leu Gly Glu
        435                 440                 445

Ala His Leu Ala Leu Ala Gly Lys Pro Leu His Phe His Ser
    450                 455                 460

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggaattccat atgagtgacg aattgaccta cgacctt                              37

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggaattctta tgagtggaag tgcaggggtt tgcc                                 34
```

US 8,546,113 B2

HYDROGEN PEROXIDE-FORMING NADH OXIDASE AND DNA ENCODING THE SAME

CROSS-REFERENCE TO RELATED APPLICATIONS

The present application is a 35 U.S.C. §371 National Stage patent application of International patent application PCT/JP2009/050601, filed on Jan. 9, 2009, which claims priority to Japanese patent application JP 2008-008062, filed on Jan. 17, 2008.

TECHNICAL FIELD

The present invention relates to reduced nicotinamide adenine dinucleotide (NADH) oxidase and a method for producing the same. More specifically, the present invention relates to NADH oxidase useful for, for example, determination of NADH that can be obtained from a microorganism belonging to the genus *Brevibacterium* by oxidizing NADH in a substrate-specific manner in the presence of oxygen molecules ($O_2$) so as to generate hydrogen peroxide ($H_2O_2$), and a method for producing the same.

BACKGROUND ART

Enzymes capable of regenerating a reduced coenzyme (NADH) to result in an oxidized coenzyme ($NAD^+$) are very useful because a variety of alcohols can be oxidized when such enzymes are used in combination with redox enzymes. There are different reports on NADH oxidase (see Patent Documents 1 to 11).

Patent Document 1: JP Patent Publication (Kokai) No. 7-163378 A (1995)
Patent Document 2: JP Patent Publication (Kokai) No. 2003-116585 A
Patent Document 3: WO2004/011670
Patent Document 4: EP 1285962
Patent Document 5: JP Patent Publication (Kokai) No. 8-196281 A (1996)
Patent Document 6: EP 623677
Patent Document 7: JP Patent Publication (Kokai) No. 5-344890 A (1993)
Patent Document 8: JP Patent Publication (Kokai) No. 5-84072 A (1993)
Patent Document 9: JP Patent Publication (Kokai) No. 4-365478 A (1992)
Patent Document 10: EP 385415
Patent Document 11: JP Patent Publication (Kokai) No. 2-107186 A (1990)

DISCLOSURE OF THE INVENTION

It is an object of the present invention to provide DNA encoding novel NADH oxidase from a microorganism belonging to the genus *Brevibacterium* having excellent pH stability and thermostability.

There are many known oxidases isolated from a variety of microorganisms. However, there have been no examples of oxidases isolated from microorganisms belonging to the genus *Brevibacterium*.

In general, the optimum pH of a redox enzyme that causes an alcohol oxidization reaction is approximately 9 to 10, indicating that the pH is weakly alkaline. Therefore, it is desired that the optimum pH of NADH oxidase used for regeneration to result in $NAD^+$ fall within the above range. However, the optimum pH of *Lactobacillus*-derived NADH oxidase (patent granted to Evonik Degussa GmbH) is approximately 6, which is not appropriate for an $NAD^+$-regenerating enzyme. In addition, an $NAD^+$-regenerating enzyme is required to have high thermostability.

The present inventors conducted intensive studies in order to obtain an enzyme having such excellent features. As a result, the present inventors have found that NADH oxidase from a microorganism belonging to the genus *Brevibacterium* (newly separated by the present inventors) has an optimum pH on the alkaline side and high thermostability. This has led to the completion of the present invention.

Specifically, the present invention is described as follows.

[1] NADH oxidase from a microorganism belonging to the genus *Brevibacterium* having the following enzymological features of:
(1) catalyzing an NADH oxidization reaction with the use of oxygen as a receptor so as to form $NAD^+$ and hydrogen peroxide;
(2) having an optimum pH of approximately 8 to 10;
(3) being not deactivated even under heat treatment at 70° C. for 1 hour and having a residual activity of 80% or more;
(4) having an optimum temperature of 50° C. to 70° C.;
(5) being activated by an ammonium salt; and
(6) having a molecular weight of 50 to 60 kDa when subjected to determination by SDS-PAGE.

[2] The enzyme according to [1], further having the following enzymological features of:
(7) having a low degree of NADPH-oxidizing activity and not being activated by FAD or FMN; and
(8) having a Km value of approximately 0.022 mM.

[3] The NADH oxidase according to [1] or [2], which is from *Brevibacterium* sp. KU1309 (accession number: FERM P-21008).

[4] A method for producing the NADH oxidase according to any one of [1] to [3], comprising culturing a microorganism belonging to the genus *Brevibacterium* and collecting NADH oxidase from the culture.

[5] The method for producing the NADH oxidase according to [4], wherein the microorganism belonging to the genus *Brevibacterium* is *Brevibacterium* sp. KU1309 (accession number: FERM P-21008).

[6] NADH oxidase from a microorganism belonging to the genus *Brevibacterium* that is the following (a) or (b):
(a) NADH oxidase comprising the amino acid sequence of SEQ ID NO: 18; or
(b) NADH oxidase comprising an amino acid sequence derived from the amino acid sequence of SEQ ID NO: 18 by deletion, substitution, or addition of 1 or more amino acid(s) and having NADH oxidase activity.

[7] DNA encoding NADH oxidase from a microorganism belonging to the genus *Brevibacterium* that is the following (a) or (b):
(a) NADH oxidase comprising the amino acid sequence of SEQ ID NO: 18; or
(b) NADH oxidase comprising an amino acid sequence derived from the amino acid sequence of SEQ ID NO: 18 by deletion, substitution, or addition of 1 or more amino acid(s) and having NADH oxidase activity.

[8] DNA encoding NADH oxidase from a microorganism belonging to the genus *Brevibacterium* that is the following (c) or (d):
(c) DNA having the nucleotide sequence of SEQ ID NO: 17
(d) DNA hybridizing DNA having a sequence complementary to DNA having the nucleotide sequence of SEQ ID NO: 17 under stringent conditions and encoding a protein having NADH oxidase activity.

[9] An expression vector containing the DNA according to [8].

[10] A host cell transformed with the expression vector according to [9].

[11] A method for producing NADH oxidase, comprising culturing the host cell according to [10] under conditions that allow DNA expression, causing generation of NADH oxidase, and collecting the NADH oxidase.

[12] The method according to [11], wherein the host cell is *Escherichia coli* in which a chaperone plasmid is co-expressed with the use of the expression vector according to [9] for production of soluble NADH oxidase.

[13] A method for producing optically active mandelic acid or D-phenylalanine with the use of the NADH oxidase according to any one of [1] to [3] and [6].

This description includes part or all of the contents as disclosed in the description and/or drawings of Japanese Patent Application No. 2008-008062, which is a priority document of the present application.

BRIEF DESCRIPTION OF THE DRAWINGS

FIG. 1B shows SDS-PAGE results for the enzyme of the present invention.

FIG. 2 shows a pH profile of the enzyme of the present invention.

FIG. 3 shows pH stability of the enzyme of the present invention.

FIG. 5A shows effects of different salts upon the enzyme of the present invention.

FIG. 5B shows effects of an ammonium salt upon the enzyme of the present invention.

FIG. 6 shows results of inhibition of the enzyme of the present invention with the use of acids.

FIG. 10 shows results of degenerate PCR for cloning of the enzyme gene of the present invention.

FIG. 13A shows the nucleotide sequence of the enzyme gene of the present invention. FIG. 13A discloses nucleotides 1-450 of SEQ ID NO: 17 and residues 1-150 of SEQ ID NO: 18, respectively, in order of appearance.

FIG. 13B shows the nucleotide sequence of the enzyme gene of the present invention (continued from FIG. 13A). FIG. 13B discloses nucleotides 451-945 of SEQ ID NO: 17 and residues 151-315 of SEQ ID NO: 18, respectively, in order of appearance.

FIG. 13C shows the nucleotide sequence of the enzyme gene of the present invention (continued from FIG. 13B). FIG. 13C discloses nucleotides 946-1,619 of SEQ ID NO: 17 and residues 316-462 of SEQ ID NO: 18, respectively, in order of appearance.

FIG. 14 shows the structures of plasmids used for expression of the enzyme of the present invention in a recombinant *Escherichia coli*.

BEST MODE FOR CARRYING OUT THE INVENTION

Figure 1A:
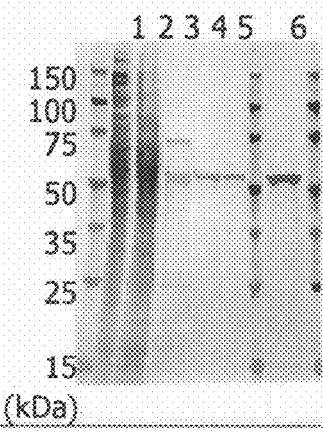
FIG. 1A shows results of purification of the enzyme of the present invention with the use of a Butyl toyopearl column.

The enzyme of the present invention can be isolated from a microorganism belonging to the genus *Brevibacterium* living in soil. Isolation of microorganisms belonging to the genus *Brevibacterium* can be carried out by known methods. An example of a microorganism belonging to the genus *Brevibacterium* is *Brevibacterium* sp. KU1309. *Brevibacterium* sp. KU1309 has been deposited with the International Patent Organism Depository, the National Institute of Advanced Industrial Science and Technology (AIST Tsukuba Central 6, 1-1-1 Higashi, Tsukuba, Ibaraki, Japan) as of Aug. 29, 2006 (accession number: FERM P-21008).

Mycological characteristics of *Brevibacterium* sp. KU1309 are described below.

(a) Morphology
(1) *Bacillus* exhibiting a rod-coccus cycle with the following cell size: 0.8×1.0 to 1.5 µm (24 h) or 0.8×0.8 to 1.0 µm (72 h)
(2) Gram stainability: Positive
(3) Presence or absence of spores: None
(4) Motility: None
(5) Colony morphology (medium: Nutrient Agar; culture time: 24 hours):
    round, continuously smooth circumference, slightly convex, shiny, and yellowish
(6) Growing temperature: 37° C. (+) or 45° C. (−)
(7) Catalase: Positive
(8) Oxidase: Negative
(9) Acid/gas generation (glucose): −/−
(10) O/F test (glucose): −/−

In addition, SEQ ID NO: 1 represents a 16S rDNA nucleotide sequence.

Based on the above mycological characteristics, *Brevibacterium* sp. KU1309 of the present invention has been identified as a new microorganism.

The enzyme of the present invention can be purified as an NADH oxidase having higher alcohol-oxidizing activity than the above culture of a microorganism. A microorganism can be cultured by known methods. For instance, a microorganism can be cultured with the use of a medium containing an ordinary bouillon (20 g) (Kyokuto Pharmaceutical Industrial Co., Ltd.) and yeast extract (5 g) (Kyokuto Pharmaceutical Industrial Co., Ltd.). It is possible to culture a microorganism described above for 1 to 2 days, disrupt microbial cells, and then purify the enzyme of the present invention from the microbial cell extract. Also, the enzyme of the present invention can be purified by a known method. For instance, a cell extract is obtained by disrupting microbial cells via ultrasonic disruption, mechanical disruption (with the use of glass beads), or with the use of a French press, a surfactant, a lytic enzyme, or the like. Then, such extract can be purified by a salting-out method with the use of ammonium sulfate or salt cake, a metal condensation method with the use of magnesium chloride or calcium chloride, a condensation method with the use of protamine or an ethyleneimine polymer, heat treatment, ion-exchange chromatography, or the like. For example, purification may be carried out using a Butyl toyopearl column (Tosoh Corporation).

The enzyme activity of the enzyme of the present invention can be determined by measuring the absorbance at 340 nm, which decreases when NADH is oxidized to result in $NAD^+$, with an absorption spectrometer. The amount of enzyme that allows 1μ mole of NADH to be oxidized in 1 minute is designated as "1 unit (U)."

The enzyme of the present invention is referred to as "NOX" in some cases.

NADH oxidase of the present invention has characteristics described below.

(1) The enzyme of the present invention catalyzes an NADH oxidization reaction with the use of oxygen as a receptor so as to form $NAD^+$ and hydrogen peroxide by the following reaction formula:

$$NADH + H^+ + O_2 \rightarrow NAD^+ + H_2O_2.$$

(2) The optimum pH of the enzyme of the present invention is approximately 8 to 10, which is preferable for an oxidization reaction of alcohol with a redox enzyme.
(3) The enzyme of the present invention has excellent thermostability. The enzyme is not deactivated even under heat treatment at 70° C. for 1 hour and has a residual activity of 80% or more, preferably 90% or more, and further preferably substantially 100%. Such characteristics are preferable for the substance production process.
(4) The optimum temperature for the enzyme of the present invention is 50° C. to 70° C. and preferably approximately 60° C.
(5) The enzyme of the present invention is activated with an ammonium salt. It is preferable to use ammonia water in order to keep the reaction system weakly alkaline, resulting in enzyme activation.
(6) The enzyme of the present invention is inhibited by a mild acid such as $Zn^{2+}$ (39%), $Cu^{2+}$ (42%), or $Ag^+$ (37%).
(7) The enzyme of the present invention has a low degree of NADPH-oxidizing activity and is not activated by FAD or FMN. The enzyme of the present invention is characterized in that it cannot oxidize NADPH. This is an advantageous feature that allows selective determination of the amount of NADH in a biological sample containing both NADH and NADPH.
(8) The Km value of the enzyme of the present invention is 0.1 mM or less and preferably approximately 0.02 mM (for example, 0.022 mM).
(9) When the enzyme of the present invention is used for oxidization of 1 mol of NADH, 1 mol of hydrogen peroxide is formed.
(10) The enzyme of the present invention is in the form of a homodimer. The molecular weight of the subunit determined by SDS-PAGE is 50 kDa to 60 kDa, and preferably approximately 57 kDa. The molecular weight of a homodimer estimated by gel filtration is approximately 102 kDa. In addition, the molecular weight of the subunit estimated based on the amino acid sequence is approximately 49 kDa.

FIG. 13 and SEQ ID NO: 17 show the nucleotide sequence of the enzyme of DNA encoding the present invention. In addition, FIG. 13 and SEQ ID NO: 18 show the amino acid sequence of the enzyme of the present invention.

The enzyme of the present invention may have a mutation such as a deletion, substitution, or addition of at least 1 and preferably 1 or more amino acid(s) in the amino acid sequence as long as a protein comprising the amino acid sequence has NADH oxidase enzyme activity.

For example, at least 1 and preferably 1 or more amino acid(s) (e.g., 1 to 10 and more preferably 1 to 5 amino acid(s)) may be deleted from the amino acid sequence of SEQ ID NO: 18. At least 1 and preferably 1 or more amino acid(s) (e.g., 1 to 10 and more preferably 1 to 5 amino acid(s)) may be added to the amino acid sequence of SEQ ID NO: 18. Alternatively, at least 1 and preferably 1 or more amino acid(s) (e.g., 1 to 10 and more preferably 1 to 5 amino acid(s)) may be substituted with different amino acids in the amino acid sequence of SEQ ID NO: 18.

Examples of such amino acid sequence derived from the amino acid sequence of SEQ ID NO: 18 by deletion, substitution, or addition of 1 or more amino acid(s) include an amino acid that is found to have at least 85% or more, preferably 90% or more, further preferably 95% or more, and particularly preferably 97% or more homology to the amino acid sequence of SEQ ID NO: 18 as a result of calculation with the use of, for example, BLAST (Basic Local Alignment Search Tool of the National Center for Biological Information) (e.g., a default parameter (i.e., an initial setting parameter)).

Such protein having an amino acid sequence derived from the amino acid sequence of SEQ ID NO: 18 by deletion, substitution, or addition of 1 or more amino acid(s) is substantially identical to a protein having the amino acid sequence of SEQ ID NO: 18.

In addition, DNA of the present invention includes DNA encoding a protein having NADH oxidase activity that can hybridize to DNA having a sequence complementary to the nucleotide sequence of SEQ ID NO: 17 under stringent conditions described below. Specifically, the term "stringent conditions" used herein refers to the conditions for hybridization at 68° C. in the presence of 0.7 to 1.0 M NaCl with the use of a DNA binding filter and washing at 68° C. with a 0.1- to 2-fold concentrated SSC solution (1-fold concentrated SSC comprising 150 mM NaCl and 15 mM sodium citrate) that allow identification of DNA. Alternatively, DNA of the present invention includes DNA that can form a hybrid after being transcribed into a nitrocellulose membrane by Southern blotting, fixed, and then subjected to a reaction overnight at 42° C. in hybridization buffer (50% formamide, 4×SSC, 50 mM HEPES (pH 7.0), 10×Denhardt's solution; and salmon sperm DNA (100 μg/ml)).

Also, the present invention encompasses RNA corresponding to the above RNA or RNA encoding a protein having NADH oxidase activity and being capable of hybridizing to the above RNA under stringent conditions.

The recombinant vector of the present invention can be obtained by ligating (or inserting) DNA of the present invention to/into an appropriate vector. A vector into which DNA of the present invention is inserted is not particularly limited as long as it can be duplicated in a host cell such as a bacterial, yeast, or animal cell. Examples thereof include plasmid DNA and phage DNA. A widely popular vector DNA that can be readily obtained is used for construction of an expression vector. Examples of vectors include a pET vector, a pQE vector, a pCold vector, and a pUC19 vector.

A method for constructing the expression vector of the present invention is not particularly limited, and therefore a general method can be applied.

A host cell that is transformed by the expression vector of the present invention is not particularly limited as long as the DNA of the present invention can be expressed. However, examples thereof include: bacteria such as *Escherichia coli* and *Bacillus subtilis*; yeasts such as *Saccharomyces cerevisiae*; and animal cells such as Chinese hamster ovary (CHO) cells, monkey COS cells, and mouse fibroblast cells.

The present invention encompasses a method for producing NADH oxidase, comprising culturing a host cell containing the above DNA under conditions that allow expression of the DNA so as to cause generation of NADH oxidase and collecting the NADH oxidase.

When the enzyme of the present invention is abundantly expressed in *Escherichia coli*, protein folding does not proceed smoothly. This tends to result in production of an inclusion body in an insoluble fraction. Therefore, it is preferable to co-express the enzyme of the present invention with a chaperone plasmid in *Escherichia coli* so as to promote solubilization by a chaperone. Examples of chaperone plasmids include pGro7, pKJE7, and pTf16.

NADH oxidase produced by a host cell can be purified by using, alone or in combination, known purification methods such as gel filtration chromatography, ultrafiltration, ion-exchange chromatography, affinity chromatography, hydrophobic chromatography, chromatofocusing, isoelectric focusing, and gel electrophoresis.

The enzyme of the present invention can regenerate a reduced coenzyme (NADH) that is necessary for an oxidization reaction in the form of oxidized coenzyme (NAD$^+$). A variety of alcohols can be oxidized using the enzyme of the present invention in combination with a different redox enzyme. In addition, it is possible to produce optically active (S)-mandelic acid and optically active D-phenylalanine by, for example, carrying out a coupling reaction with the combined use of the enzyme of the present invention and mandelate dehydrogenase or L-phenylalanine dehydrogenase. Further, the enzyme of the present invention can be used for an $H_2O_2$ quantification method for determination of activity of a different dehydrogenase with the use of NADH and for determination of the amount of substrate for a different dehydrogenase with the use of NAD as a coenzyme. Moreover, the applied use of the enzyme of the present invention for biofuel cells and enzyme diagnostic agents can be expected.

The present invention is hereafter described in greater detail with reference to the following examples, although the technical scope of the present invention is not limited thereto.

EXAMPLE 1

Enzyme Purification (1) Cell Culture

*Brevibacterium* sp. KU1309, which is a microorganism belonging to the genus *Brevibacterium*, was isolated from soil and cultured by the method described below. Isolated *Brevibacterium* sp. KU1309 was deposited with the International Patent Organism Depository, the National Institute of Advanced Industrial Science and Technology (AIST Tsukuba Central 6, 1-1-1 Higashi, Tsukuba, Ibaraki, Japan) as of Aug. 29, 2006 (accession number: FERM P-21008).

A medium containing ordinary bouillon (20 g) (Kyokuto Pharmaceutical Industrial Co., Ltd.) and yeast extract (5 g) (Kyokuto Pharmaceutical Industrial Co., Ltd.) dissolved therein (per litter) was adjusted to pH 7.0 with 2M sodium hydroxide and subjected to heat sterilization at 120° C. for 20 minutes. The resulting medium was used for culture.

The medium (10 ml) placed in a test tube was inoculated with *Brevibacterium* on a solid medium with the use of a platinum loop, followed by shake culture at 30° C. for 24 hours. The cell suspension (1 ml) was added to a 500-ml Sakaguchi flask containing the above medium (100 ml), followed by shake culture at 30° C. for 24 hours. The cells were collected by centrifugation. The obtained cells were washed with a phosphate buffer and again collected by centrifugation. Long-term preservation of such cells at −20° C. is possible.

(2) Enzyme Purification

Cell-Free Extract Preparation

Moist cells (20 g) were suspended in a 100 mM phosphate buffer (pH 7.0) containing 5 mM 2-mercaptoethanol and then disrupted using a Dyno-mill (Willy A. Bachofen Co.). The obtained mixture was centrifuged. The supernatant was collected and designated as a cell-free extract.

(3) Enzyme Activity Determination

Enzyme activity was evaluated by measuring the absorbance at 340 nm, which decreases as a result of oxidization of NADH to NAD$^+$, with the use of an absorptiometer. A reaction was induced by adding an enzyme solution to a mixture of 0.1 mM NADH, 100 mM Tris-HCL (pH 8.8), and 500 mM ammonium sulfate. Herein, "1 unit" is defined as the amount of an enzyme that allows oxidation of 1μ mole of NADH per minute.

(4) Ammonium Sulfate Fractionation

Ammonium sulfate was added little by little during agitation at 0° C. for 15 minutes to the cell-free extract so as to result in a concentration corresponding to 35% saturation. Then, the mixture was further agitated for 1 hour. The precipitate was removed therefrom by centrifugation. Ammonium sulfate was added for 15 minutes to the supernatant so as to result in 65% saturation. After the completion of the addition, the mixture was agitated for 1 hour. Then, the precipitate was collected therefrom by centrifugation. The precipitate was dissolved in a 10 mM phosphate buffer (pH 7.0) containing a 10 mM phosphate buffer, 5 mM 2-mercaptoethanol, and 30% saturated ammonium sulfate.

(5) Chromatography

A sample was introduced into a Phenyl toyopearl column (Tosoh Corporation; column volume: 150 ml) equilibrated with a 10 mM phosphate buffer containing 5 mM 2-mercaptoethanol and saturated 30% ammonium sulfate (=buffer A), followed by chromatography with the use of an Econo Gradient Pump (Bio Rad) (flow rate: 1.5 ml/min.). The column was washed with buffer A (450 ml). Protein elution was performed with an ammonium sulfate linear gradient from buffer A (450 ml) to 10 mM phosphate buffer B containing 5 mM 2-mercaptoethanol and 20% saturated ammonium sulfate (pH 7.0) (450 ml). The enzyme activity of each fraction was examined. Active fractions were collected and subjected to dialysis with a 10 mM phosphate buffer (pH 7.0). The fraction pool was introduced into a DEAE toyopearl column (Tosoh Corporation; column volume: 50 ml) equilibrated with a 10 mM phosphate buffer containing 5 mM 2-mercaptoethanol and 200 mM NaCl (pH 7.0) (buffer C), followed by washing with buffer C (150 ml). Protein elution (flow rate: 1 ml/min.) was performed with an NaCl linear gradient from buffer C (150 ml) to a 10 mM phosphate buffer containing 5 mM 2-mercaptoethanol and 300 mM NaCl (pH 7.0) (150 ml) (=buffer D). Active fractions were collected from the resultant. Ammonium sulfate was added thereto so as to result in 30% saturation. The obtained solution was introduced into a Butyl toyopearl column (Tosoh Corporation; column volume: 10 ml) equilibrated with a 10 mM phosphate buffer containing 5 mM 2-mercaptoethanol and 30% saturated ammonium sulfate (pH 7.0) (=buffer E), followed by washing with buffer E (30 ml). Thereafter, protein elution (flow rate 1 ml/min.) was performed with an ammonium sulfate linear gradient from buffer E (30 ml) to a 10 mM phosphate buffer containing 5 mM 2-mercaptoethanol and 15% saturated ammonium sulfate (pH 7.0) (30 ml) (=buffer F). Active fractions were collected and subjected to dialysis with a 10 mM phosphate buffer (pH 7.0). FIG. 1B shows the enzyme activity of each fraction obtained using a Butyl toyopearl column. As shown in FIG. 1A, a single peak was observed. Further, purification and then SDS-PAGE were carried out. As a result of staining with CBB, uniform bands were confirmed at approximately 50 kDa (56.8 kDa) (FIG. 1A). In addition, as a result of gel filtration chromatography, the molecular weight of the enzyme in a nondenatured state was found to be 102 kDa, indicating an enzyme existing in a dimer form. In addition, the color of the purified enzyme solution was transparent yellow. Therefore, the obtained enzyme was thought to be a flavin enzyme (flavoenzyme).

Table 1 summarizes enzyme activity and yield in the purification process.

TABLE 1

Enzyme activity and yield in the purification process

| | Volume (ml) | Total activity (U) | Total protein amount (mg) | Specific activity (U/mg) | Degree of purification | Yield (%) |
|---|---|---|---|---|---|---|
| Cell-free extract | 205 | 69.09 | 800.98 | 0.086 | 1.00 | 100 |
| Ammonium sulfate fraction | 78 | 33.31 | 466.69 | 0.071 | 0.83 | 48 |
| Phenyl toyopearl | 75 | 15.68 | 16.55 | 0.947 | 10.98 | 23 |
| DEAE toyoperal | 42 | 9.73 | 2.31 | 4.212 | 48.83 | 14 |
| Butyl toyoperal | 12 | 7.04 | 1.35 | 5.215 | 60.46 | 10 |

EXAMPLE 2

Enzymological Characteristics of NADH Oxidase Isolated from *Brevibacterium* sp.

(1) pH Dependency

The optimum pH for an oxidization reaction was determined to be within the range of pH 5.5 to 11.5. Buffer appropriate for the relevant pH range was used. Specifically, MES (pH 5.5 to 6.5), MOPS (pH 6.5 to 7.4), HEPES (pH 7.0 to 8.0), Tris (pH 7.5 to 8.8), glycine (pH 8.8 to 10.4), CAPS (pH 9.4 to 10.8), or sodium phosphate (pH 10.54 to 11.52)) was used. FIG. 2 summarizes the relative reaction rate at the corresponding pH.

The enzyme of the present invention was found to have an optimum pH on the alkaline side (pH 8.5 to 10).

(2) pH Stability

The enzyme was incubated at 70° C. for 1 hour at a pH in the range of pH 4.5 to 11.5, followed by residual activity determination. The following buffers were used: citric acid (pH 4.7), MES (pH 5.5, 6.3), MOPS (pH 6.6, 7.4), Tris (pH 7.4, 8.5), TAPS (pH 8.4, 9.2), CAPS (pH 9.4, 10.2), and sodium phosphate (pH 10.5, 11.5).

FIG. 3 shows results of plotting residual activity, provided that the residual activity determined without heating at 70° C. was designated as 100%.

As shown in the figure, the activity was stable in a wide pH range of pH 6 to 10.

(3) Thermostability

Figure 4:
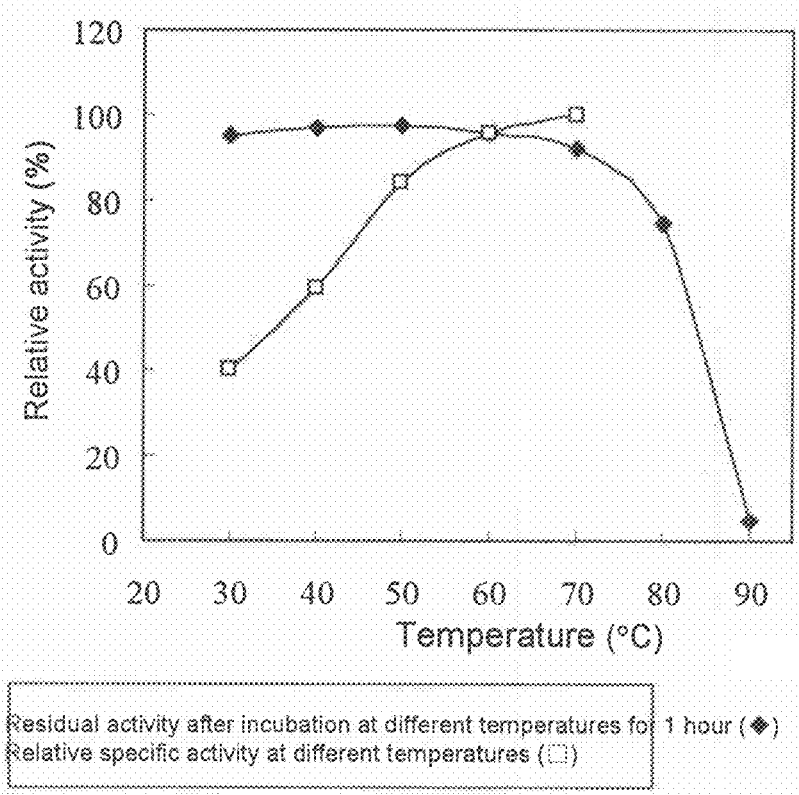
FIG. 4 shows thermostability of the enzyme of the present invention.

Thermostability in MOPS buffer (pH 6.6) was examined. Incubation was carried out for 1 hour at each predetermined temperature. Then, the activity was determined at room temperature. The results are shown with the symbol "♦" in the graph of FIG. 4. The enzyme activity was determined at the relevant temperatures (30° C. to 70° C.). The results are shown with the symbol "□" in the graph of FIG. 4.

As shown in the figure, the activity was stable with an almost 100% certainty during incubation at 70° C. for 1 hour.

(4) Effects of Salts

Reaction was carried out with the addition of different salts, followed by determination of absorbance at 340 nm. Then, the reaction rate was determined. FIG. 5A shows effects of different salts upon enzyme activity. It was found that the enzyme activity increases with the addition of an ammonium salt as described above. Then, the effects of ammonium salt concentration upon enzyme activity were examined in the manner described below. The reaction was carried out in the presence of ammonium sulfate at a concentration of 0 M to 4.35 M. Thereafter, the relative value of the reaction rate was calculated. FIG. 5B shows effects of ammonium salt upon enzyme activity.

As shown in the figure, ammonium salts are necessary to increase activity. The maximum activity was achieved at an ammonium salt concentration ($[NH_4^+]$) of 3.0 M.

(5) Inhibitory Experiments

The enzyme solution was added to 100 mM Tris-HCl (pH 8.8). Further, an inhibitor was added thereto to a final concentration of 1 mM, followed by incubation at room temperature for 3 minutes. Then, NADH and $(NH_4)_2SO_4$ were added thereto so as to result in concentrations of 10 μM and 500 mM, respectively, followed by determination of the absorbance at 340 nm. Accordingly, the reaction rate was determined.

FIG. 6 shows relative activity values. As shown in FIG. 6, the activity was inhibited with a mild acid such as $Zn^{2+}$ (39%), $Cu^{2+}$ (42%), or $Ag^+$ (37%).

(6) Kinetic Analysis

For kinetic analysis, the reaction rate was determined at an NADH concentration of 10 μM to 100 μM. A Lineweaver-Burk plot was created based on the obtained values. The reaction was carried out as described below. A reaction solution (NOX: 0.28 ug/ml; NADH: 10 μM to 100 μM; $(NH_4)_2SO_4$: 500 mM; and Tris-HCl: 100 mM (pH 8.8)) was introduced into an absorptiometer cell, followed by determination of the absorbance at 340 nm. Accordingly, the reaction rate was determined.

Figure 7:
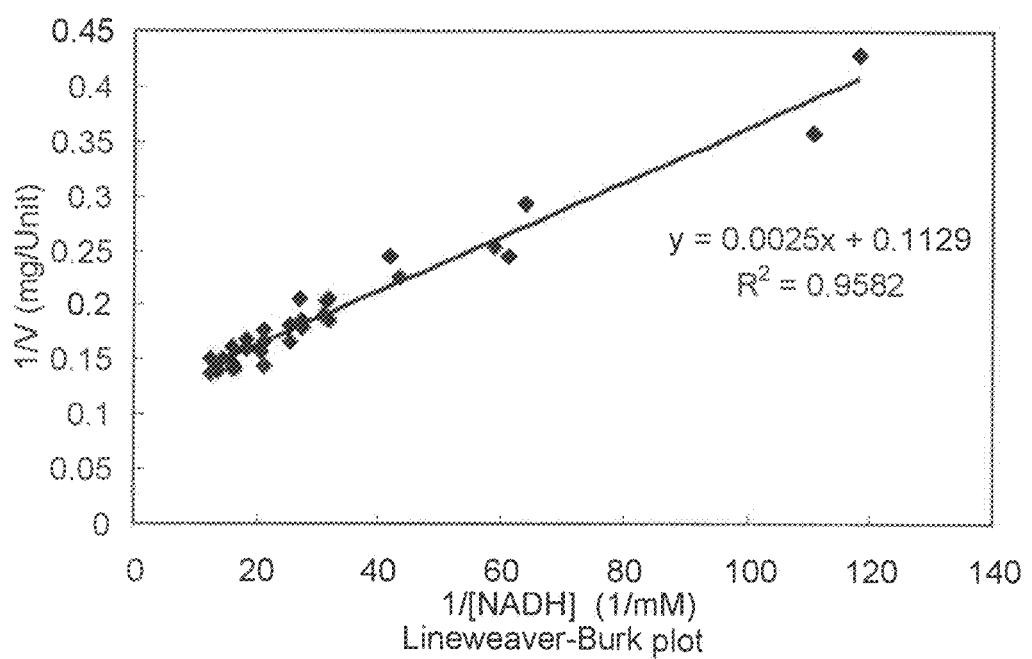
FIG. 7 shows the kinetics of the enzyme of the present invention.

FIG. 7 shows results of Lineweaber-Burk plotting.

Table 2 shows kinetics in the presence of NADH.

TABLE 2

Kinetics in the presence of NADH

| Km | (mM) | 0.022 |
|---|---|---|
| Vmax | (Unit/mq) | 8.86 |
| Kcat* | (1/sec) | 15.01 |
| Kcat/Km | | 677.87 |

*Calculated with a molecular weight of 101.68 kDa

Table 3 lists substrates and activity levels in the presence of cofactors.

TABLE 3

| Substrate | Cofactor | Specific activity (%) |
|---|---|---|
| NADH | NONE | 100 |
| | 1 mM FAD | 101 |
| | 1 mM FMN | 104 |
| NADPH | | 2 |

The Km of the enzyme of the present invention was as 0.022 mM, which was very low. In addition, the degree of NADPH-oxidizing activity was low. Further, activation caused by FAD or FMN was not observed.

(7) The State of Oxygen Molecules Reduced by the Enzyme

Figure 8A:
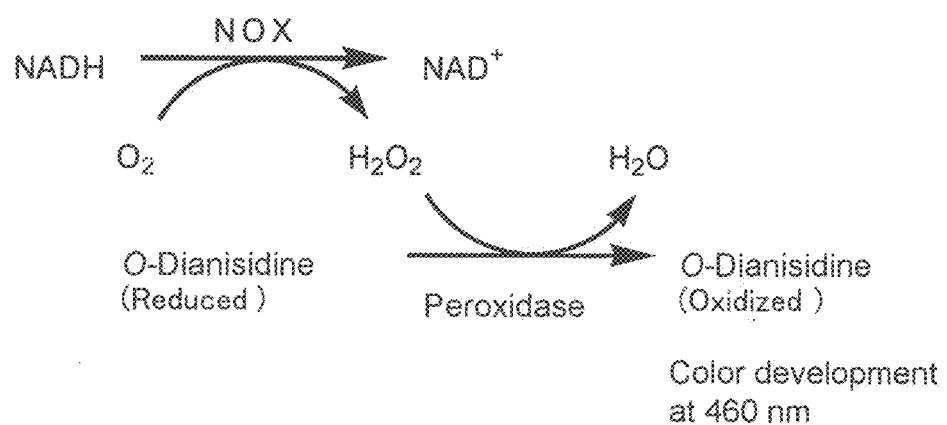
FIG. 8A shows a method for determining the state of an oxygen molecule reduced by the enzyme of the present invention.

NOX is classified into the $H_2O$ by-product type and the $H_2O_2$ by-product type. With the use of the assay method shown in FIG. 8A, $H_2O_2$ formation confirmation and $H_2O_2$ quantification were carried out.

Figure 8B:
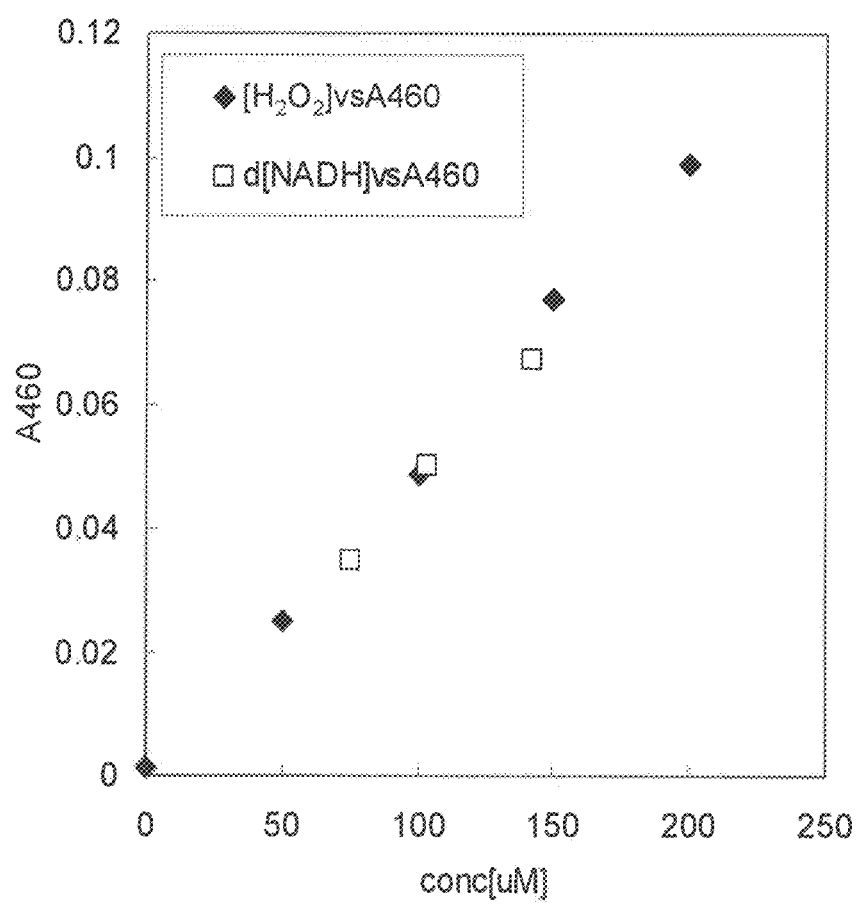
FIG. 8B shows the state of an oxygen molecule reduced by the enzyme of the present invention.

First, the reaction was carried out with the use of hydrogen peroxide, o-dianisidine, and peroxidase at known concentrations. The standard curve of $[H_2O_2]$ vs Abs460 was created. The symbol "♦" denotes each obtained plotted point on the curve in FIG. 8B. Next, an NADH oxidation reaction was actually carried out with the use of NOX, followed by determination of the concentration of hydrogen peroxide formed as a result of the reaction. Specifically, the NOX-induced oxidization reaction was carried out at NADH concentrations of 75 µM, 100 µM, and 150 µM. The reaction was completed after the elapse of a sufficient reaction time. The completion of the reaction was confirmed with the use of an absorptiometer. The obtained reaction solution (50 µl) was added to a 100 mM phosphate buffer (pH 7.0) containing o-dianisidine and peroxidase, followed by absorbance determination. The symbol "□" denotes each obtained plotted point on the curve in FIG. 8B. The plotted points represent Abs 460 values at NADH concentrations of 75, 100, and 150 µM from the left. It is understood that the values were identical to the relevant $[H_2O_2]$ concentrations.

Accordingly, $H_2O_2$ formation was confirmed. In addition, it was found that oxidization of 1 mol of NADH results in formation of 1 mol of hydrogen peroxide.

EXAMPLE 3

Example of the Use of NADH Oxidase (i) Preparation of Optically Active Mandelic Acid with the Use of Mandelate Dehydrogenase Mandelic acid was oxidized with the combined use of mandelate dehydrogenase from *Enterococcus faecalis* IAM 10071 (Tamura, Y., et al. 2002. Appl. Environ. Microbiol. 68: 957-957) and NADH oxidase from *Brevibacterium* sp.

Mandelate dehydrogenase was subjected to simple purification before use in the manner described below.

An MRS medium (10 ml) placed in a test tube was inoculated with *Enterococcus faecalis* IAM 10071 collected from a solid medium with the use of a platinum loop, followed by shake culture at 30° C. for 24 hours. The total amount of the culture solution was transferred to a 5-liter Erlenmeyer flask (with a baffle) containing an MRS medium (1.2 liter), followed by rotation culture at 30° C. for 48 hours. Cells were collected from the culture solution by centrifugation. Thus, moist cells (9.2 g) were obtained. The cells were suspended in 100 mM Tris-HCL buffer (pH 7.5) containing 5 mM 2-mercaptoethanol, followed by disruption of the cells with the use of a mill. Undisrupted cells were removed therefrom by centrifugation such that a cell-free extract was obtained. For the enzyme activity of mandelate dehydrogenase, the absorbance of NADH formed as a result of oxidization of mandelic acid was determined at 340 nm with the use of an absorptiometer. The reaction was carried out with the addition of the enzyme solution to a mixture of 50 mM racemic mandelic acid, 1 mM $NAD^+$, and 100 mM Tris-HCL (pH 8.8). Proteins precipitated with 25%- to 60%-saturated ammonium sulfate were collected by centrifugation and dissolved in 10 mM Tris-HCL buffer (pH 7.5), followed by dialysis with the same buffer. The obtained enzyme solution was introduced into a DEAE toyopearl column (column volume: 50 ml; flow rate: 1 ml/min.) equilibrated with 10 mM Tris-HCL (pH 7.5) containing 5 mM 2-mercaptoethanol and 100 mM NaCl, followed by washing with the equilibrated buffer. Protein elution was performed with a linear gradient from an equilibrated buffer (150 ml) to 10 mM Tris-HCL containing 5 mM 2-mercaptoethanol and 200 mM NaCl (pH 7.5) (150 ml). Active fractions were collected from the resulting fraction, followed by concentration with the use of Amicon Ultra (MILLIPORE). Thus, partially purified enzyme of mandelate dehydrogenase was obtained.

The reaction with the combined use of mandelate dehydrogenase and NADH oxidase was carried out using the following composition. A mixture of 2 mM racemic mandelic acid, 0.1 mM $NAD^+$, 250 mM ammonium sulfate, 100 mM Tris-HCL (pH 8.8), 0.1 U/ml NADH oxidase, and 0.1 U/ml mandelate dehydrogenase was incubated at 30° C. for determination of the optical purity of mandelic acid by HPLC [HPLC conditions: CHIRALCEL OD-H (DAICEL CHEMICAL INDUSTRIES, LTD.); development phase: hexane/isopropyl alcohol (=19/1) and 0.2% trifluoroacetic acid; flow rate: 0.5 ml/min.; detection UV: 254 nm; and retention time: 22.14 min. for (S)-mandelic acid and 27.23 min. for (R)-mandelic acid]

Figure 9A:
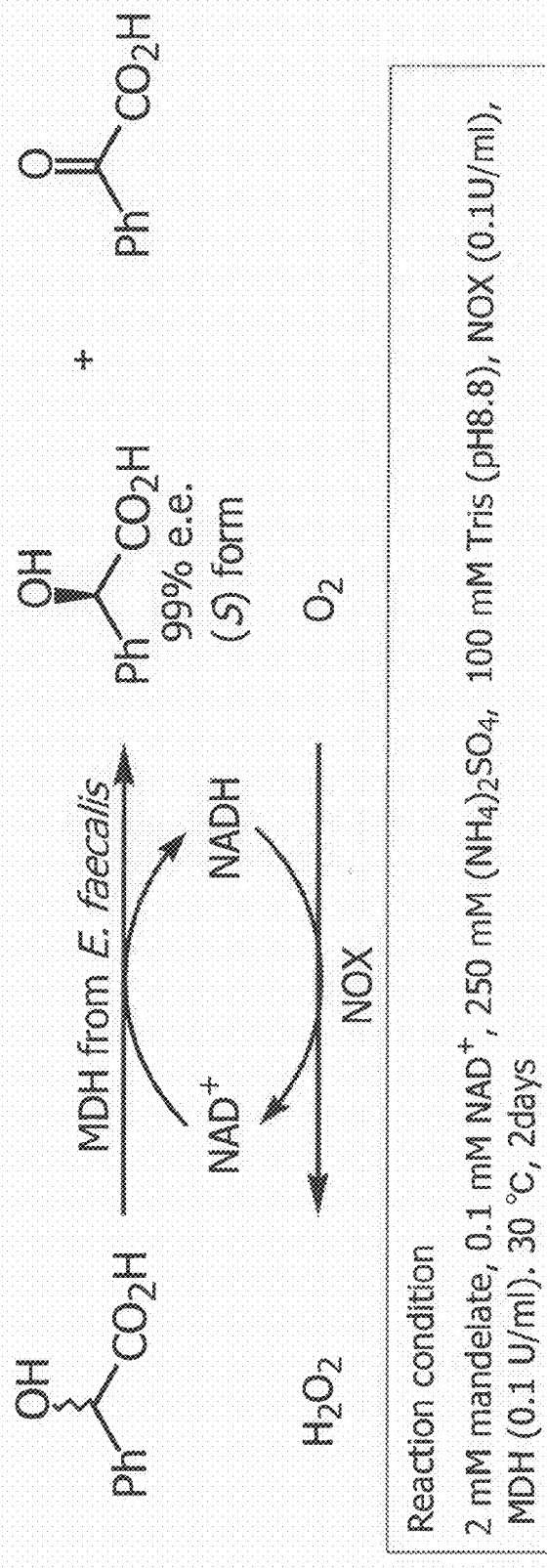
FIG. 9A is a diagram showing a coupling reaction of the enzyme of the present invention and mandelate dehydrogenase.

FIG. 9A shows the reaction mechanism of a coupling reaction of the enzyme of the present invention and mandelate dehydrogenase.

As a result, the total amount of (R)-mandelic acid was oxidized 48 hours later. Accordingly, optically active (S)-mandelic acid was obtained.

(ii) Preparation of D-Phenylalanine with the Use of L-Phenylalanine Dehydrogenase L-phenylalanine dehydrogenase herein used was purchased from Wako Pure Chemical Industries, Ltd.

The reaction was carried out in accordance with the following composition. A mixture of 2.5 mM DL phenylalanine, 0.1 mM $NAD^+$, 10 mM ammonium sulfate, 100 mM CAPS (pH 10.2), 0.2 U/ml NADH oxidase, and 0.2 U/ml L-phenylalanine dehydrogenase was incubated at 30° C. Then, the optical purity of phenylalanine in the system was examined by HPLC [HPLC conditions: Crownpak CR (+); development phase: 5.7% perchloric acid; flow rate: 0.5 ml/min.; detection UV: 200 nm; retention time: 18.5 min. for D-phenylalanine and 25.1 min. for L-phenylalanine]

Figure 9B:
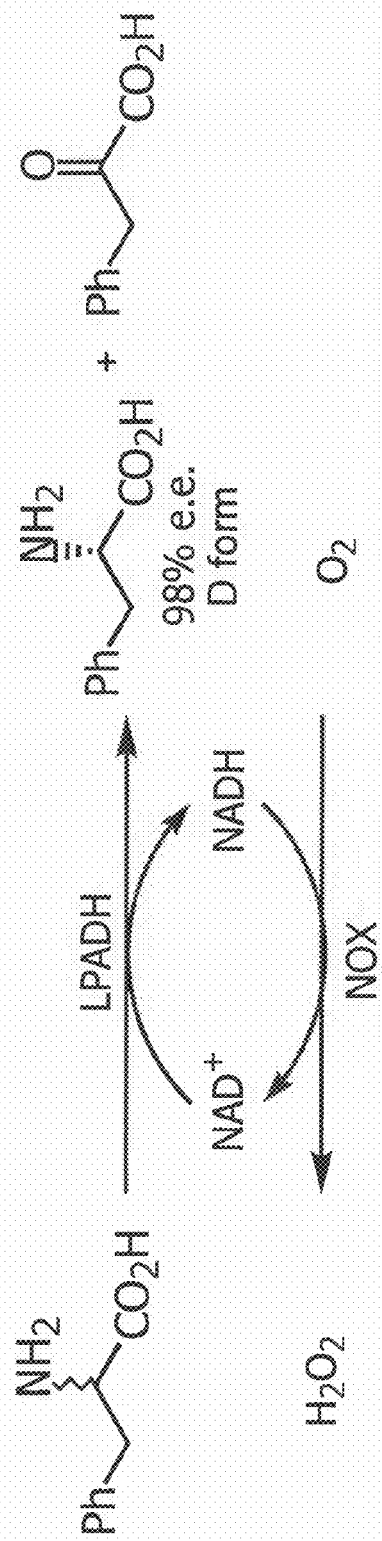
FIG. 9B is a diagram showing a coupling reaction of the enzyme of the present invention and L-phenylalanine dehydrogenase.

FIG. 9B shows the reaction mechanism of the coupling reaction of the enzyme of the present invention and L-phenylalanine dehydrogenase.

As a result, the total amount of L-phenylalanine was oxidized 48 hours later. Accordingly, optically active D-phenylalanine was obtained.

As described above, since NADH oxidase from *Brevibacterium* sp. has a wide range of pH characteristics (especially on the weak alkali side) and high stability, it is thus highly versatile.

EXAMPLE 4

Enzyme Gene Cloning

For cloning of the isolated enzyme gene, the N-terminal amino acid sequence and the internal amino acid sequence were analyzed. Then, fragments were obtained by PCR with the use of degenerate primers and cloning of the full-length gene sequence was carried out by inverse PCR. The details are described below.

N-Terminal Amino Acid Sequence

The enzyme purified in the manner described in Example 1 was subjected to SDS-PAGE. Transcription from acrylamide gel to a PVDF membrane was conducted with the use of a semi-dry blotting apparatus. The film was stained with CBB, followed by analysis of a target band with a protein sequencer. Accordingly, the N-terminal of the enzyme was found to have the following sequence:

```
XDELTYDLVVLGGGTGG.          (SEQ ID NO: 2)
```

Internal Amino Acid Sequence

The enzyme purified in the manner described in Example 1 was subjected to SDS-PAGE. After SDS-PAGE, CBB staining was carried out and a target band was excised, followed by in-gel digestion. First, it was attempted to digest the band with lysyl endopeptidase. However, it was difficult to degrade the band into peptide fragments. The observed HPLC peak was thought to be derived from a large fragment that had not been sufficiently cleaved. Therefore, digestion was attempted with the use of trypsin. Trypsin is an enzyme that cleaves the C terminal of lysine and of arginine. Therefore, it was expected that the enzyme would more finely digest the band into fragments than in a case involving the use of lysyl endopeptidase. As a result, fragmentation was successfully carried out. When the obtained fragment was analyzed with a protein sequencer, the fragment was found to have the following sequence:

```
GPVTEGFGFEEQGIPMDR.         (SEQ ID NO: 3)
```

Degenerate PCR

Based on the obtained N-terminal sequence and the internal sequence, degenerate sense primers (F01 and F02) and antisense primers (R01 and R02) described below were designed.

```
                                    (SEQ ID NO: 4)
NOX degenerate primer F01 corresponding to
DELTYDLVVL
                                    (SEQ ID NO: 5)
5'-GAYGARYTIACITAYGAYYTIGTIGTNYT-3'

(SEQ ID NO: 6)
NOX degenerate primer F02 corresponding to
VLGGGTGGY
                                    (SEQ ID NO: 7)
5'-AARYTIGGNGGIGGNACIGGIGGNTA-3'

(SEQ ID NO: 8)
NOX degenerate primer R01 corresponding to
PVTEGFGFE
                                    (SEQ ID NO: 9)
5'-TCRAANCCRAAICCYTCIGTNACNGG-3'

(SEQ ID NO: 10)
NOX degenerate primer R02 corresponding to
TEGFGFEEQ
                                    (SEQ ID NO: 11)
5'-TCCATIGGDATNCCYTGYTCYTCRAA-3'
```

The reaction was carried out in accordance with the composition and the procedure listed in Table 4 with the use of the following primer combinations: (F01×R01), (F01×R02), (F02×R01), and (F02×R02). First, it was attempted to carry out the reaction with the use of genomic DNA as a template. However, it was impossible to stabilize amplification, resulting in a small amount of the amplified product. Therefore, the reaction was carried out with the use of an EcoRI digest or a PstI digest. Accordingly, in the case of a reaction with the use of an EcoRI digest, it was able to obtain a DNA fragment with a size of approximately 800 b.p., as shown in lane 5 in FIG. 10. In this case, inosine was used to prevent an excessive increase in the degree of degeneration. In FIG. 10, lanes 1 to 4 show results obtained with the use of a PstI digest as a template. Also, lane 5 and the following lanes show results obtained with the use of an EcoRI digest as a template. The primer combinations for lanes 1 and 5, lanes 2 and 6, lanes 3 and 7, and lanes 4 and 8 were F01×R01, F01×R02, F02×R01, and F02×R02, respectively.

TABLE 4

| Reaction solution composition | |
|---|---|
| 10 × ExTaq buffer | 10 μL |
| dNTP mix | 8 μL |
| 100 μM F primer | 2 μL |
| 100 μM R primer | 2 μL |
| Genome DNA digested by EcoR1 | 1 μL |
| Ex Taq | 0.5 μL |
| DW | Up to 100 μL |

| Thermal cycle | |
|---|---|
| 1. 94° C. | 2 min. |
| 2. 94° C. | 30 sec. |
| 3. 40° C. | 30 sec. |
| 4. 72° C. | 70 sec. |
| Return to 2 and repeat 34 cycles | |

The obtained DNA fragment was purified and ligated to a pGEM (registered trademark) T-easy vector (16° C., 30 min.). XL10-Gold (Z competent cells) were transformed and applied to an LB agar medium containing ampicillin. Colony direct PCR was carried out to confirm the presence of an insert, followed by extraction of a plasmid (pGEMNOXin) from a positive clone. The obtained plasmid was subjected to sequence analysis with the use of an M13 primer. Accordingly, an 825-b.p. internal gene sequence was identified.

Southern Hybridization

Figure 11:
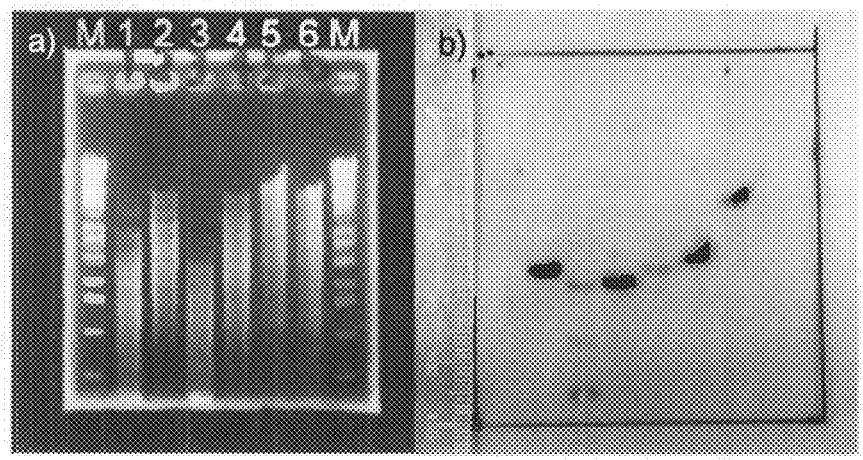
FIG. 11 shows results of Southern blotting with the use of fragments of the enzyme gene of the present invention.

Southern hybridization was carried out with the use of the obtained gene fragment. The internal sequence of the enzyme was excised from pGEMNOXin with the use of NotI, followed by purification. The resultant was used as a probe for genomic Southern hybridization. Hybridization was carried out with shaking overnight at 55° C. In addition, primary washing was also carried out at 55° C. FIG. 11 shows the results. In FIG. 11, (a) indicates results of UV detection of a genome digest and (b) indicates results of detection by enzyme fermentation. The samples used were a SalI digest, a SacI digest, a HincII digest, a XhoI digest, a Bg/I digest, and a SmaI digest for lanes 1 to 6, respectively. The letter "M" represents a marker. A fragment with a size of approximately 3000 b.p. was detected in the SalI digest.

Inverse PCR

The SalI digest of genomic DNA was subjected to agarose gel separation. A portion with a size of 2.0 k b.p. to 3.4 k b.p. was excised, purified, and dissolved in TE. Thus, a DNA fragment solution (20 ng/μL) was obtained. Water (80 μL) and 2×Ligation high (TOYOBO) (100 μL) were added to the solution (20 μL). The mixture was allowed to stand still overnight at 16° C. The resulting solution was purified and used as a TE solution (50 μl) for inverse PCR. For inverse PCR, the following primers were used in combination.

```
NOX inverse primer F01:
                                    (SEQ ID NO: 12)
5'-ACGGTGCAGGCAGGTGCCTCCCACCTTGTC-3'

NOX inverse primer F02:
                                    (SEQ ID NO: 13)
5'-GCGTTCGATCAAAGCGACCTTCATGTCGAG-3'
```

-continued

```
NOX inverse primer R01:
                                    (SEQ ID NO: 14)
5'-GGCGTCATGTTCAAGGGCGTCGAAGAGACG-3'

NOX inverse primer R02:
                                    (SEQ ID NO: 15)
5'-GCCGACGGGGTCAAGGTCACTCTCGAAGAC-3'
```

The reaction was carried out in accordance with the composition and the procedure listed in Table 5.

TABLE 5

| Reaction solution composition | |
|---|---|
| 10 × ExTaq buffer | 10 μL |
| dNTP mix | 8 μL |
| 100 μM NOX inverse primer F | 1 μL |
| 100 μM NOX inverse primer R | 1 μL |
| Template | 20 μL |
| Ex Taq | 0.5 μL |
| DW | Up to 100 μL |

| Thermal cycle | |
|---|---|
| 1. 94° C. | 2 min. |
| 2. 94° C. | 30 sec. |
| 3. 45° C. | 30 sec. |
| 4. 72° C. | 5 min. |
| Return to 2 and repeat 34 cycles | |

Figure 12:
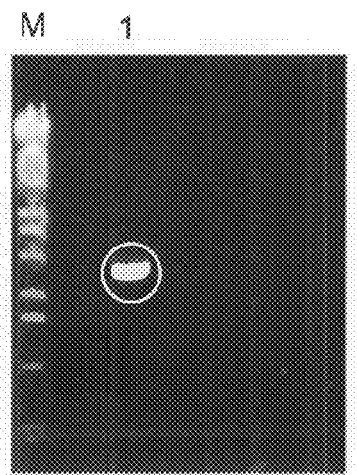
FIG. 12 shows results of inverse PCR with the use of the enzyme gene of the present invention.

FIG. 12 shows the results. As shown in FIG. 12, a DNA fragment with a size of approximately 2.6 k b.p. was obtained with the following combination of primers: F02×R02. The obtained fragment was excised by agarose gel electrophoresis, followed by purification. The obtained PCR product was subjected to sequence analysis with the use of an NOX inverse primer (F02) and an NOX inverse primer (R02) so as to analyze the degenerated N-terminal portion and a gene sequence with a size of up to 1300 b.p. For analysis of a sequence to the C terminal, the full-length gene of nox was identified with the use of primers.

```
NOX sequence 2:
5'-TCCGTCGGACTCTCCTCTGCACAG-3'   (SEQ ID NO: 16)
```

The fragment was subjected to sequence analysis such that the total nucleotide sequence encoding the purified enzyme was obtained. As a result of gene sequence analysis, the enzyme was found to be an enzyme with a mass of 48909.99 daltons comprising 462 amino acid residues. FIGS. 13A to 13C show sequence analysis results. In addition, SEQ ID NO: 17 represents the nucleotide sequence and SEQ ID NO: 18 represents the amino acid sequence.

EXAMPLE 5

Construction of the Abundant Expression System with the Use of a Recombinant *Escherichia coli* from *Brevibacterium* Sp. KU1309-Derived NADH Oxidase The abundant expression of the enzyme of the present invention was examined with the use of *Escherichia coli*.

Gene Preparation

Primers are designed as described below with the use of the *Brevibacterium* sp. KU1309 genome as a template, provided that valine (GTG) at the N-terminal was substituted with methionine (ATG).

```
NOXForNde01:
                                    (SEQ ID NO: 19)
5'-GGAATTCCATATGAGTGACGAATTGACCTACGACCTT-3'

(The underlined portion denotes the NdeI site.)

NOXRevEco01:
                                    (SEQ ID NO: 20)
5'-GGAATTCTTATGAGTGGAAGTGCAGGGGTTTGCC-3'

(The underlined portion denotes EcoRI and the set
of Italic alphabets denotes a termination codon.)
```

PCR was carried out in accordance with the composition and the procedure listed in Table 6 with the use of the primers and a genomic DNA (SalI) digest of KU1309 as a template.

TABLE 6

| Reaction solution composition | |
|---|---|
| 10 × ExTaq buffer | 10 μL |
| dNTP mix | 8 μL |
| 100 μM NOXForNde01 | 1 μL |
| 100 μM NOXRevEco01 | 1 μL |
| Template | 0.5 μL |
| Ex Taq | 0.5 μL |
| DW | Up to 100 μL |

| Thermal cycle | |
|---|---|
| 1. 94° C. | 2 min. |
| 2. 94° C. | 30 sec. |
| 3. 50° C. | 30 sec. |
| 4. 72° C. | 2.5 min. |
| Return to 2 and repeat 34 cycles | |

Vector Construction

The obtained gene (nox gene) was incorporated into pET21-b (+) and pCold III such that plasmids pET21BNOX and pCBNOX were prepared. pET21BNOX was inserted into a vector in a manner such that wild BNOX was expressed under the control of a T7 promoter and pCBNOX was inserted into a vector in a manner such that TEE-fused BNOX was expressed under the control of a cold shock promoter (FIG. 14).

Examination of Expression

Expression in a variety of hosts was examined using the constructed plasmid vectors. Expression induction was carried out for several hours after culture of a host at 37° C. and the addition of IPTG. The obtained microbial cells were subjected to ultrasonic disruption, followed by determination of NADH-oxidizing activity in the supernatant. Even in a case in which IPTG was not added, *Escherichia coli* itself had NOX activity. Therefore, the systems capable of exhibiting a significant difference compared with the case of the IPTG-free sample were examined. Table 7 shows the results.

TABLE 7

| Vector | Host | IPTG (mM) | Temperature (° C.) | Expression | Specific activity* (U/mg) |
|---|---|---|---|---|---|
| pET21BNOX | BL21(DE3) | 1 | 25 | ○ | 0.036 |
| | | 0.5 | 16 | ○ | 0.028 |
| | | 0.3 | 10 | ○ | 0.026 |

TABLE 7-continued

| Vector | Host | IPTG (mM) | Temperature (° C.) | Expression | Specific activity* (U/mg) |
|---|---|---|---|---|---|
| | BL21star(DE3)pLysS | 0.5 | 15 | X | 0 |
| | Tuner(DE3) | 0.3 | 25 | ○ | 0 |
| | Rosetta-gamiB(DE3) | 0.3 | 25 | X | 0 |

*Calculated based on the difference between the activity in the sample to which IPTG was added and the activity in the IPTG-free sample.

Figure 15:
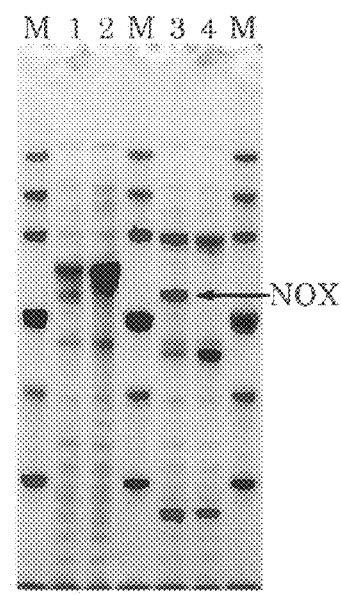
FIG. 15 shows expression of the enzyme of the present invention (soluble fraction) as a result of co-expression with chaperone.

As shown in Table 7, abundant expression was observed in some hosts. However, inclusion body formation took place in most of the hosts. Therefore, in order to solve this problem, *Escherichia coli* into which a chaperone plasmid had been introduced was used for expression induction. Based on the results of the above examination, it was decided that BL21 (DE3) confirmed to have expressed a soluble active enzyme would be used as *Escherichia coli*. Table 8 shows the results. Further, FIG. 15 shows SDS-PAGE results. In FIG. 15, lane 1 shows expression with pGro7 (with expression induction), lane 2 shows expression with pGro7 (without expression induction), lane 3 shows expression with pKJE7 (with expression induction), and lane 4 shows expression with pKJE7 (without expression induction).

TABLE 8

| Vector | Host | Chaperone plasmid | Expression | Specific activity (U/mg) |
|---|---|---|---|---|
| pET21BNOX | BL21(DE3) | pGro7 | ○ | 0.073 |
| | | pKJE7 | ○ | 0.076 |
| | | pG-KJE8 | Δ | 0 |
| | | pTf16 | ○ | 0.0017 |

As shown in Table 8, when pGro7 or pKJE7 was used, the activity was improved. In addition, as shown in FIG. 15, expression induction was successfully carried out to such an extent that the expression was possible to visually confirm in a soluble fraction.

INDUSTRIAL APPLICABILITY

The NADH oxidase of the present invention has excellent pH stability and thermostability and therefore can be very useful as an essential coenzyme-regenerating enzyme whereby a highly efficient reaction process can be realized.

All publications, patents, and patent applications cited herein are incorporated herein by reference in their entirety.

The invention claimed is:

1. A method for producing optically active mandelic acid or D-phenylalanine with an isolated NADH oxidase consisting of the amino acid sequence of SEQ ID NO:18 from a microorganism belonging to the genus *Brevibacterium* comprising the following enzymological features of:

(1) catalyzing an NADH oxidization reaction comprising oxygen as a receptor so as to form NAD$^+$ and hydrogen peroxide;

(2) having an optimum pH of approximately 8 to 10;

(3) being not deactivated even under heat treatment at 70° C. for 1 hour and having a residual activity of 80% or more;

(4) having an optimum temperature of 50° C. to 70° C.;

(5) being activated by an ammonium salt;

(6) having a molecular weight of 50 to 60 kpa when subjected to determination by SDS-PAGE, (7) having a low degree of NADPH-oxidizing activity and not being activated by FAD or FMN; and (8) having a Km value of approximately 0.022 mM.

* * * * *